United States Patent [19]
Joly et al.

[11] Patent Number: 5,789,199
[45] Date of Patent: *Aug. 4, 1998

[54] PROCESS FOR BACTERIAL PRODUCTION OF POLYPEPTIDES

[75] Inventors: John C. Joly, San Mateo; James R. Swartz, Menlo Park, both of Calif.

[73] Assignee: Genentech, Inc., South San Francisco, Calif.

[ * ] Notice: The term of this patent shall not extend beyond the expiration date of Pat. No. 5,639,635.

[21] Appl. No.: 741,727

[22] Filed: Oct. 31, 1996

Related U.S. Application Data

[63] Continuation-in-part of Ser. No. 333,912, Nov. 3, 1994, Pat. No. 5,639,635.

[51] Int. Cl.$^6$ ............................................. C12N 15/63
[52] U.S. Cl. ............... 435/69.1; 435/252.3; 435/252.33; 935/11; 935/43
[58] Field of Search .................. 435/69.1, 252.3, 435/252.33; 935/11, 43

[56] References Cited

U.S. PATENT DOCUMENTS

| | | | |
|---|---|---|---|
| 5,270,181 | 12/1993 | McCoy et al. | 435/69.7 |
| 5,292,646 | 3/1994 | McCoy et al. | 435/69.7 |
| 5,304,472 | 4/1994 | Bass et al. | 435/69.1 |

FOREIGN PATENT DOCUMENTS

| | | |
|---|---|---|
| 293793 A2 | 12/1988 | European Pat. Off. . |
| 509841 | 10/1992 | European Pat. Off. . |
| 510658 | 10/1992 | European Pat. Off. . |
| 60-38771 | 2/1994 | Japan . |
| WO 93/25676 | 12/1993 | WIPO . |
| WO 94/08012 | 4/1994 | WIPO . |

OTHER PUBLICATIONS

Bardwell et al., "The Bonds That Tie: Catalyzed Disulfide Bond Formation" *Cell* 74:769–771 (1993).
Bardwell et al., "Identification of a Protein Required for Disulfide Bond Formation In Vivo" *Cell* 67:581–589 (1991).
Bardwell et al., "A pathway for disulfide bond formation in vivo" *Proc. Natl. Acad. Sci* 90:1038–1042 (1993).
Bulleid, Neil J., "Protein Disulfide–Isomerase: Role in Biosynthesis of Secretory Proteins" *Adv. Prot. Chem.* 44:125–150 (1993).
Chivers et al., "The CXXC Motif: Imperatives for the Formation of Native Disulfide Bonds in the Cell" *The EMBO Journal* 15(11):2659–2667 (1996).
Creighton et al., "Catalysis by Protein–disulphide Isomerase of the Unfolding and Refolding of Proteins with Disulphide Bonds" *J. Mol. Biol.* 142:43–62 (1980).
Freedman et al., "Role of Protein Disulphide–Isomerase in the Expression of Native Proteins" *Biochem. Soc. Symp.* 55:167–192 (1989).
Grauschopf et al., "Why is DsbA Such an Oxidizing Disulfide Catalyst?" *Cell* 83:947–955 (1995).
Kamitani et al., "Identification and characterization of an *Escherichia coli* gene required for the formation of correctly folded alkaline phosphatase, a periplasmic enzyme" *The EMBO Journal* 11(1):57–62 (1992).

Knappik et al., "The Effect of Folding Catalysts on the In Vivo Folding Process of Different Antibody Fragments Expressed in *Escherichia coli* " *Bio/Technology* 11:77–83 (1993).
LaMantia et al., "The Essential Function of Yeast Protein Disulfide Isomerase Does Not Reside in Its Isomerase Activity" *Cell* 74:899–908 (1993).
Martin et al., "Crystal structure of the DsbA protein required for disulphide bond formation in vivo" *Nature* 365:464–468 (1993).
Missiakas et al., "The *Escherichia coli* dsbC (xprA) gene encodes a periplasmic protein involved in disulfide bond formation" *The EMBO Journal* 3(8):2013–2020 (1994).
Missiakas et al., "Identification and characterization of the *Escherichia coli* gene dsbB, whose product is involved in the formation of disulfide bonds in vivo" *Proc. Natl. Acad. Sci.* 90:7084–7088 (1993).
Noiva et al., "Protein Disulfide Isomerase" *Journal of Biological Chemistry* 267(6):3553–3556 (1992).
Shevchik et al., "Characterization of DsbC, a periplasmic protein of *Erwinia chrysanthemi* and *Escherichia coli* with disulfide isomerase activity" *The EMBO Journal* 13(8):2007–2012 (1994).
Wulfing et al., "Correctly Folded T–cell Receptor Fragments in the Periplasm of *Escherichia coli* " *J. Mol. Biol.* 242:655–669 (1994).
Wulfing et al., "Protein folding in the periplasm of *Escherichia coli* " *Molecular Microbiology* 12(5):685–692 (1994).
Wunderlich et al., "In Vivo Control of Redox Potential During Protein Folding Catalyzed by Bacterial Protein Disulfide–isomerase (DsbA)" *Journal of Biological Chemistry* 268(33):24547–24550 (1993).
Wunderlich et al., "Redox properties of protein disulfide isomerase (DsbA) from *Escherichia coli* " *Protein Science* 2:717–726 (1993).
Zapun et al., "The Reactive and Destabilizing Disulfide Bond of DsbA, a Protein Required for Protein Disulfide Bond Formation in Vivo" *Biochemistry* 32:5083–5092 (1993).

*Primary Examiner*—Elizabeth C. Kemmerer
*Assistant Examiner*—Brian Lathrop
*Attorney, Agent, or Firm*—Janet E. Hasak

[57] ABSTRACT

A process is provided for producing a heterologous polypeptide in bacteria. This process comprises, in a first step, culturing bacterial cells that lack their native pstS gene and comprise nucleic acid encoding a PstS variant having an amino acid variation within the phosphate-binding region of the corresponding native PstS, nucleic acid encoding a DsbA or DsbC protein, nucleic acid encoding the heterologous polypeptide, a signal sequence for secretion of both the DsbA or DsbC protein and the heterologous polypeptide, an inducible promoter for the nucleic acid encoding the DsbA or DsbC protein, and an alkaline phosphatase promoter for the nucleic acid encoding the heterologous polypeptide. The nucleic acid encoding a PstS variant is under the transcriptional control of the wild-type pstS gene promoter. The second step of the process involves recovering the heterologous polypeptide from the periplasm or the culture medium.

32 Claims, 5 Drawing Sheets

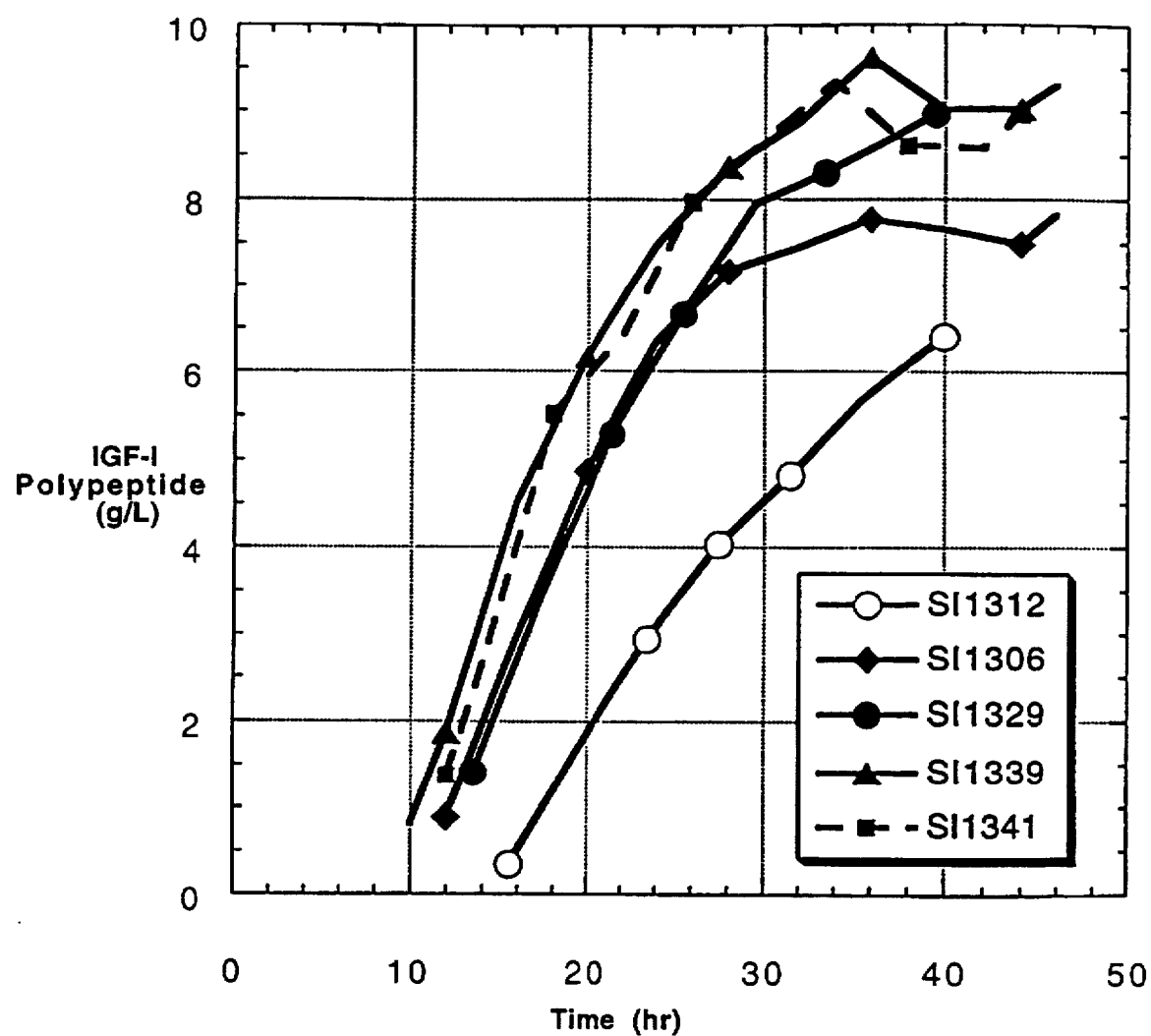

PROCESS FOR BACTERIAL PRODUCTION OF POLYPEPTIDES

This application makes reference to and claims the benefits available under 35 U.S.C. Section 120, as a continuation-in-part of U.S. Ser. No. 08/333,912, filed 3 Nov. 1994, now U.S. Pat. No. 5,639,635 the entire disclosure of which is incorporated herein by reference.

BACKGROUND OF THE INVENTION

1. Field of the Invention

This invention relates to a process for producing and secreting polypeptides in bacteria by overproduction and secretion of a DsbA or DsbC protein.

2. Description of Related Disclosures

Much research has been conducted in the field of protein folding since the seminal publication of Anfinsen et al., *Proc. Natl. Acad. Sci. USA*, 47: 1309–1314 (1961) showing that, in vitro, reduced and denatured ribonuclease could refold into the active enzyme with the formation of suitable disulfide bonds. Later, a catalyst responsible for oxidative folding in eukaryotes was discovered, called protein disulfide isomerase (PDI).

Two types of proteins that assist in protein folding have been described: non-catalytic molecular chaperones that presumably prevent improper interactions leading to aggregation and events other than proper folding, and catalysts for two steps in protein folding, cistrans prolyl isomerization and disulfide bond formation. While clear evidence for an in vivo requirement of prolyl isomerase activity is still lacking, the relatively recent isolation of mutants that are severely defective in disulfide bond formation has confirmed that this latter folding step is catalyzed in vivo.

PDI has been implicated in the catalysis of disulfide bond formation and rearrangement through in vitro data. Creighton et al., *J. Mol. Biol.*, 142: 43–62 (1980); Freedman et al., *Biochem. Soc. Symp.*, 55: 167–192 (1989). See also Bardwell and Beckwith, *Cell*, 74: 769–771 (1993). In addition, yeast mutants in PDI that fail to form disulfide bonds in carboxypeptidase Y have been identified, indicating the importance of PDI in disulfide bond formation in vivo. LaMantia and Lennarz, *Cell*, 74: 899–908 (1993).

In prokaryotes, mutations in a specific gene identified in the periplasm of *E. coli* by three independent investigating groups show a dramatic and pleiotropic decrease in the rate of disulfide bond formation in secreted proteins. The protein encoded by this gene was variously designated as DsbA (disulfide bond) by Bardwell et al., *Cell*, 67: 581–589 (1991) and Missiakas et al., *Proc. Natl. Acad. Sci. USA*, 90: 7084–7088 (1993) and as PpfA (periplasmic phosphatase/protein formation) by Kamitani et al., *EMBO J.*, 11: 57–62 (1992). It is hereinafter referred to by the Dsb designation. The secreted proteins affected by this decrease in disulfide bond formation range from proteins endogenous to *E. coli* such as alkaline phosphatase and OmpA to the recombinant mammalian proteins, urokinase and tissue plasminogen activator. It is now clear that the formation of disulfide bonds is a catalyzed process in both eukaryotes and prokaryotes. For a review on PDI and DsbA, see Bardwell and Beckwith, *Cell*, supra (1993).

The DsbA protein has a highly reactive disulfide bond, similar to disulfide isomerase. Noiva and Lennarz, *J. Biol. Chem.*, 267: 3553–3556 (1992); Bulleid, *Adv. Prot.*, 44: 125–150 (1993). Its crystal structure has recently been solved (Martin et al., *Nature*, 365: 464–468 [1993]) and its redox potential has been determined. Wunderlich and Glockshuber, *Prot. Sci.*, 2: 717–726 (1993). It is a significantly stronger oxidant than the cytoplasmic thioredoxin and it more closely resembles the eukaryotic disulfide isomerases. It was found that unfolding DsbA stabilizes the reactive disulfide bond by about 18.9 kJmol$^{-1}$. Zapun et al., *Biochemistry*, 32: 5083–5092 (1993). This result is interpreted to indicate that the disulfide bond destabilizes the folded form of DsbA, thereby conferring its high energy content.

The gene of a second protein involved in disulfide bond formation, called dsbB, was cloned by two independent groups. Bardwell et al., *Proc. Natl. Acad. Sci. USA*, 90: 1038–1042 (1993) and Missiakas et al., 1993, supra. DsbB is an integral membrane protein spanning the inner membrane. It appears to be involved in the re-oxidation of DsbA and thus may form part of a chain that links an electron transfer step to the formation of disulfide bonds in the periplasm. Bardwell et al., supra (1993). A third gene for disulfide bond formation, dsbC, was recently identified. Missiakas et al., *EMBO J.*, 13: 2013–2020 (1994); Shevchik et al., *EMBO J.*, 13: 2007–2012 (1994). It encodes a 26-kDa periplasmic protein that can functionally substitute for DsbA.

It has been shown that DsbA is required for the rapid formation of disulfide bonds of periplasmic *E. coli* proteins in vivo and in vitro. The same was found for the production of recombinant eukaryotic proteins in the periplasm of *E. coli*, e.g., different serine proteases (Bardwell et al., supra [1993]), antibody fragments (Knappik et al., *Bio/Technology*, 11: 77–83 [1993]), and fragments of a T-cell receptor. The fraction of the recombinant molecules that becomes correctly folded can be smaller than in the case of natural periplasmic proteins, and is very sequence dependent. Overproduction of DsbA did not help to increase the proportion of correctly folded periplasmic antibody fragments (Knappik et al., supra), indicating that other steps limit their folding in the periplasm. Furthermore, folding of the α-amylase/trypsin inhibitor from Ragi in the periplasm was not improved when the dsbA gene was co-expressed and DsbA protein co-secreted without reduced glutathione present in the growth medium, but an increase in correctly folded secreted inhibitor was observed by co-expression of dsbA in conjunction with the addition of reduced glutathione to the medium. Wünderlich and Glockshuber, *J. Biol. Chem.*, 268: 24547–24550 (1993). Further, Wünderlich and Glockshuber show no increase in total accumulation of the secreted α-amylase/trypsin inhibitor protein.

Wülfing and Plückthun, *Molecular Microbiology*, 12: 685–692 (1994) produced functional fragments of a T-cell receptor (TCR) in the periplasm of *E. coli* by modest overproduction of DsbA and the *E. coli* heat-shock proteins at low temperature. The latter was achieved by over-expression of rpoH, which codes for the heat-shock sigma factor, sigma$^{32}$. This increased the folding yield of the TCR fragments in the periplasm by about two orders of magnitude. It is not known what the yield is in the absence of rpoH overproduction. U.S. Pat. Nos. 5,270,181 and 5,292,646 disclose recombinant production of heterologous proteins by expression as a fusion protein with a thioredoxin-like protein (such as the thioredoxin-like domain of PDI) for high stability and solubility. JP 60-38771 published Feb. 15, 1994 discloses the expression of a human PDI gene linked to human serum albumin pre-pro sequence and co-expression of this linked gene and a foreign gene encoding a polypeptide. WO 93/25676 published Dec. 23, 1993 discloses the production of disulfide-bonded recombinant proteins using a PDI, preferably a yeast PDI. EP 293,793 published Dec. 7, 1988 discloses a polypeptide with PDI activity ensuring natural disulfide bridge arrangement in recombinant proteins. WO 94/08012 published Apr. 14, 1994 discloses increasing secretion of over-expressed gene products by co-expression of a chaperone protein such as a heat-shock protein or PDI. EP 509,841 published Oct. 21, 1992 discloses increased secretion of human serum albumin from yeast cells using a co-expression system involving PDI and a protein. U.S. Pat. No. 5,304,472 discloses use of bacterial PstS mutants in the production of heterologous polypeptides.

There is a continuing need for increasing the total yield of proteins secreted by prokaryotes.

Therefore, it is an object of this invention to provide a method for increasing polypeptide yield using an economically viable method involving physiologically regulating the intracellular environment for enhanced accumulation of foreign polypeptides in bacteria.

This object and other objects will become apparent to those skilled in the art.

SUMMARY OF THE INVENTION

Accordingly, in one aspect the present invention provides a process for producing a heterologous polypeptide in bacteria comprising:

(a) culturing bacterial cells, which cells comprise nucleic acid encoding a DsbA or DsbC protein, nucleic acid encoding the heterologous polypeptide, a signal sequence for secretion of both the DsbA or DsbC protein and the heterologous polypeptide, and an inducible promoter for both the nucleic acid encoding the DsbA or DsbC protein and the nucleic acid encoding the heterologous polypeptide, under conditions whereby expression of the nucleic acid encoding the DsbA or DsbC protein is induced prior to induction of the expression of the nucleic acid encoding the heterologous polypeptide, and under conditions whereby either both the heterologous polypeptide and the DsbA or DsbC protein are secreted into the periplasm of the bacteria or the heterologous polypeptide is secreted into the medium in which the bacterial cells are cultured; and (b) recovering the heterologous polypeptide from the periplasm or the culture medium.

In another embodiment, the invention provides a process for producing a heterologous polypeptide in bacteria comprising:

(a) culturing bacterial cells that lack their native pstS gene and comprise nucleic acid encoding a PstS variant having an amino acid variation within the phosphate-binding region of the corresponding native PstS, nucleic acid encoding a DsbA or DsbC protein, nucleic acid encoding the heterologous polypeptide, a signal sequence for secretion of both the DsbA or DsbC protein and the heterologous polypeptide, an inducible promoter for the nucleic acid encoding the DsbA or DsbC protein, and an alkaline phosphatase promoter for the nucleic acid encoding the heterologous polypeptide, wherein the nucleic acid encoding a PstS variant is under the transcriptional control of the wild-type pstS gene promoter, and wherein the culturing takes place under conditions whereby expression of the nucleic acid encoding the DsbA or DsbC protein is induced prior to induction of the expression of the nucleic acid encoding the heterologous polypeptide, under conditions whereby the culturing takes place in a culture medium at a concentration of inorganic phosphate in the medium that during all phases of cell growth is above the level at which the cells are starved for phosphate, and under conditions whereby either both the heterologous polypeptide and the DsbA or DsbC protein are secreted into the periplasm of the bacteria or the heterologous polypeptide is secreted into the medium in which the bacterial cells are cultured; and (b) recovering the heterologous polypeptide from the periplasm or the culture medium.

The over-expression and secretion of the bacterial protein DsbA or DsbC results in a significant increase in the amount of heterologous polypeptide produced in the periplasm of bacteria or in the culture medium. In the specific example shown below, the over-expression and secretion of the *E. coli* protein DsbA resulted in a large increase in the total yield of human IGF-I deposited in inclusion bodies in the periplasmic space of *E. coli*. Furthermore, this total yield increase is accomplished by culturing in the absence of any glutathione in the medium and without co-expressing or over-expressing the *E. coli* heat-shock transcription factor, RpoH.

While DsbA has been suggested to be involved in the folding of periplasmic and outer wall proteins of *E. coli*, it was not known whether over-expression of the gene encoding this protein would have any effect, by itself, on secreted human proteins. It was also not known if over-expression of the dsbA gene would result in higher levels of DsbA-associated activity. If any effect were seen, it was expected that higher levels of DsbA activity would promote the proper folding of IGF-I polypeptide and result in higher levels of folded, soluble IGF-I monomer. In contrast, a significant increase was observed in total yield of IGF-I, due to an increase in the deposition of IGF-I polypeptide into insoluble aggregates, and the yield of soluble, properly folded protein decreased. Due to the fact that efficient methods exist for folding these insoluble aggregates into bioactive polypeptide, this increase in insoluble polypeptide is a very useful result.

Further, significantly higher titers are obtained when a host with a psts mutation and an active phoA gene is combined with DsbA overexpression for the production of heterologous polypeptide.

BRIEF DESCRIPTION OF THE DRAWINGS

FIG. 5 shows the time course of IGF-I polypeptide accumulation for five fermentation experiments entitled SI1312 (open circles), SI1306 (diamonds), SI1329 (solid circles), SI1339 (diamonds), and SI1341 (squares). Table 4 contains further details on each run.

DETAILED DESCRIPTION OF THE PREFERRED EMBODIMENTS

A. Definitions

Figure 1:
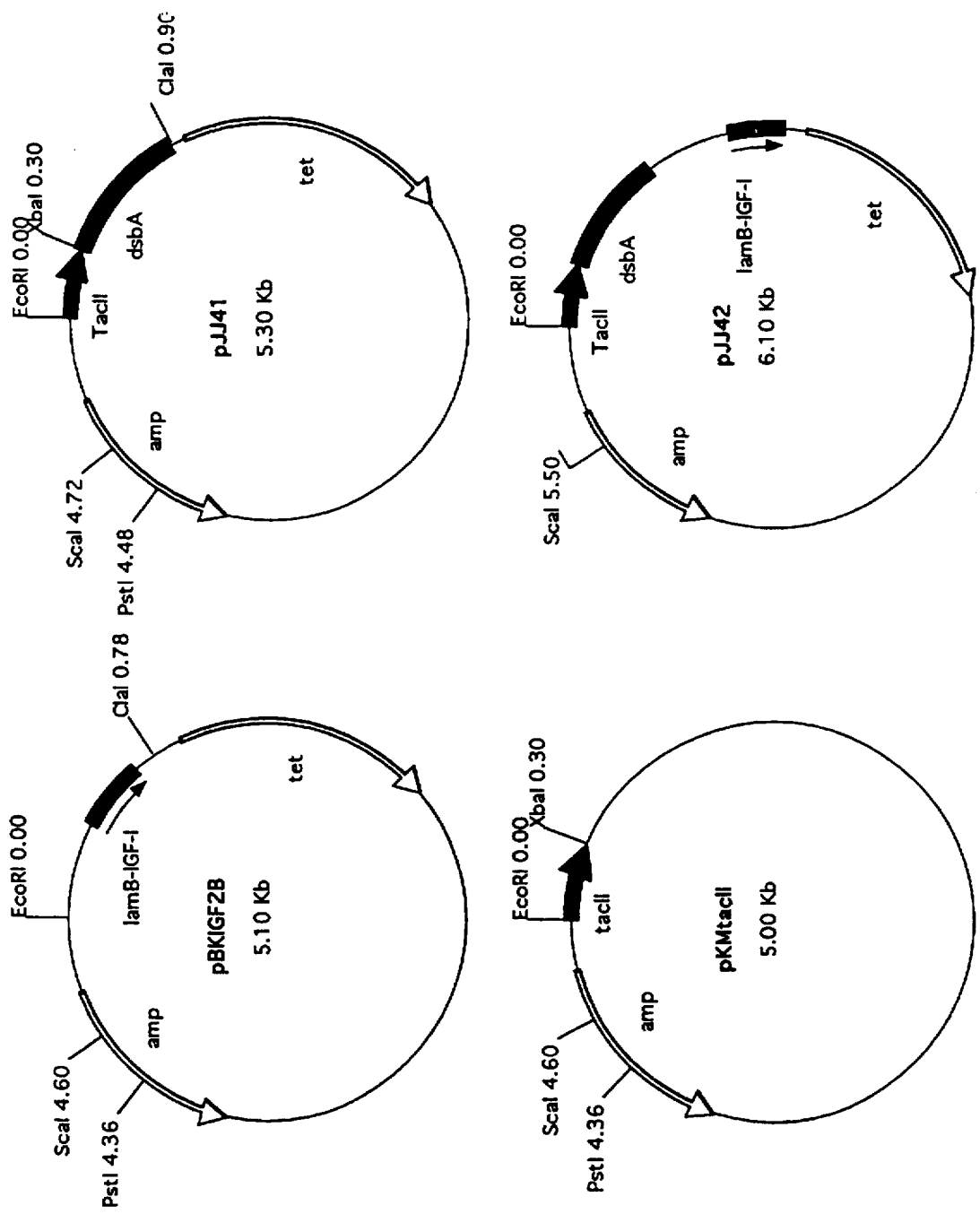
FIG. 1 depicts plasmids employed in the construction of pJJ42, used to produce IGF-I, namely pBKIGF-2B, pJJ41, and pKMtacII.

As used herein, "dsbA" and "dsbC" refer to genes encoding the bacterial periplasmic proteins known in the literature as DsbA or DsbC proteins, respectively. They may be from any bacterial source, with one example being the dsbA gene from *E. coli* as described by Bardwell et al., supra (1991) and Kamitani et al., supra, and the dsbC gene from *E. coli* as described by Missiakas et al., 1994, supra. The dsbA and dsbC genes and their products as used herein do not include PDI or any other eukaryotic protein that functions as a protein disulfide isomerase, including those disclosed in U.S. Pat. Nos. 5,270,181 and 5,292,646; JP 60-38771; WO 93/25676; EP 293,793; WO 94/08012; and EP 509,841, all supra. DsbA and DsbC differ in many respects from PDI. For example, DsbA and DsbC retain their isomerase activity in the absence of redox buffer, whereas PDI requires a redox buffer for its isomerase activity. Further, DsbA and DsbC have molecular weights by sequence analysis of 21 kD and 25 kD, respectively, and contain two and four cysteine residues, respectively, whereas PDI has a molecular weight by sequence analysis of 57 kD and contains six cysteine residues.

As used herein, "signal sequence" or "signal polypeptide" refers to a peptide that can be used to secrete the heterologous polypeptide into the periplasm or medium of the cultured bacteria or to secrete the DsbA or dsbC protein into the periplasm. The signals for the heterologous polypeptide may be homologous to the bacteria, or they may be heterologous, including signals native to the polypeptide being produced in the bacteria. For the dsbA and dsbC, the signal sequence is typically that which is endogenous to the bacterial cells, although it need not be as long as it is effective for its purpose.

An "over-expressed" gene product is one that is expressed at levels greater than normal endogenous expression for that gene product. It can be accomplished, e.g., by introducing a recombinant construction that directs expression of a gene product in a host cell, or by altering basal levels of expression of an endogenous gene product, e.g., by inducing its transcription.

The promoters of this invention are "inducible" promoters, i.e., promoters which direct transcription at an increased or decreased rate upon binding of a transcription factor. "Transcription factors" as used herein include any factors that can bind to a regulatory or control region of a promoter and thereby effect transcription. The synthesis or the promoter binding ability of a transcription factor within the host cell can be controlled by exposing the host to an "inducer" or removing an inducer from the host cell medium. Accordingly, to regulate expression of an inducible promoter, an inducer is added or removed from the growth medium of the host cell.

As used herein, the phrase "induce expression" means to increase the amount of transcription from specific genes by exposure of the cells containing such genes to an effector or inducer.

An "inducer" is a chemical or physical agent which, when given to a population of cells, will increase the amount of transcription from specific genes. These are usually small molecules whose effects are specific to particular operons or groups of genes, and can include sugars, phosphate, alcohol, metal ions, hormones, heat, cold, and the like. For example, isopropylthio-β-galactoside (IPTG) and lactose are inducers of the tacII promoter, and L-arabinose is a suitable inducer of the arabinose promoter. The pho gene promoter, such as phoA and pho5, is inducible by low phosphate concentrations in the medium.

As used herein, "polypeptide" or "polypeptide of interest" refers generally to peptides and proteins having more than about ten amino acids. Preferably, the polypeptides are "exogenous," meaning that they are "heterologous," i.e., foreign to the host cell being utilized, such as a human protein produced by a CHO cell, or a yeast polypeptide produced by a mammalian cell, or a human polypeptide produced from a human cell line that is not the native source of the polypeptide.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred exogenous polypeptides of interest are mammalian polypeptides. Examples of such mammalian polypeptides include t-PA, gp120, anti-HER-2, DNase, IGF-I, IGF-II, brain IGF-I, growth hormone, relaxin chains, growth hormone releasing factor, insulin chains or proinsulin, urokinase, immunotoxins, neurotrophins, and antigens. Particularly preferred mammalian polypeptides include, e.g., t-PA, gp120(IIIb), anti-HER-2, DNase, IGF-I, IGF-II, growth hormone, NGF, NT-3, NT-4, NT-5, and NT-6, more preferably IGF, most perferably IGF-I, and the most preferred mammalian polypeptide is a human polypeptide.

As used herein, "IGF-I" refers to insulin-like growth factor from any species, including bovine, ovine, porcine, equine, and preferably human, in native sequence or in variant form and recombinantly produced. In a preferred method, the IGF-I is cloned and its DNA expressed, e.g., by the process described in EP 128,733 published Dec. 19, 1984.

The term "PstS" refers to the protein encoded by the pstS gene found in bacterial cells, especially Enterobacteriaceae cells, including *E. coli* cells. This protein is known as the phosphate-binding protein of the bacterial cells and contains a phosphate-binding region.

The "phosphate-binding region" is the region of the protein that binds to inorganic phosphate. This region includes the domain wherein hydrogen bonds form between the two molecules. In *E. coli* PstS this region is:

| Side Chains | Backbone |
|---|---|
| Thr 10 | Thr 10 |
| Ser 38 | Thr 141 |
| Asp 56 | Ser 38 |
| Arg 135 | Gly 140 |
| Ser 139 | Phe 11 |
| Thr 141 | |

This region also includes other residues that indirectly affect phosphate binding, the associated conformational shift from open to closed complex when the phosphate is bound, and/or the associated signaling pathway. Thus, mutations in residues of PstS not directly contacting the phosphate (or proteins truncated by stop codons or frame-shifts) may have similar phenotypes to mutations in residues of PstS that bind directly to the phosphate.

"PstS variants" are defined as molecules in which the amino acid sequence of the corresponding native (wild-type) PstS protein has been modified (by either a predetermined or random mutation) in the phosphate-binding region thereof, in such a way that the PstS protein no longer functions as a repressor at levels of phosphate greater than about 10 μmolar. Furlong, "Osmotic-Shock-Sensitive Transport Systems," in Neidhardt FC et al. (eds.) *Escherichia coli and Salmonella typhimurium:Cellular and Molecular Biology*, Vol. 1 (American Society for Microbiology, Washington, D.C., 1987) p. 768–796, particularly p. 772–773. Thus, the mutation reduces the affinity of the binding protein for phosphate. Amino acid sequence variants of PstS include, for example, deletions from, or insertions or substitutions of, residues within the PstS amino acid sequence shown in FIG. 1 of U.S. Pat. No. 5,304,472. Any combination of deletion, insertion, and substitution may also be made to arrive at the final construct, provided that the final construct possesses the desired property of allowing polypeptide induction by the bacterial host cell at concentrations of phosphate in the medium that are above the starvation level.

The phrase "hydrophobic residues" refers to the residues norleucine, cysteine, methionine, alanine, valine, leucine, tyrosine, phenylalanine, tryptophan, and isoleucine.

The expression "control sequences" refers to DNA sequences necessary for the expression of an operably linked coding sequence in a particular host organism. The control sequences that are suitable for bacteria include a promoter such as the alkaline phosphatase promoter, optionally an operator sequence, and a ribosome-binding site.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Production phase of cell growth" refers to the period of time during cell growth following induction of the promoter when the polypeptide of interest is being produced.

"Partially induced" as it applies to the alkaline phosphatase promoter refers to a state in which complete induction of the alkaline phosphatase promoter is not achieved, but rather only partial induction thereof. In this way, the rate of transcription of the nucleic acid desired to be expressed is controlled.

As used herein, "phosphate starvation level" or "level at which cells are starved for phosphate" refers to a concentration of inorganic phosphate (e.g., salts of phosphoric acid such as sodium phosphate, potassium phosphate, or phosphate associated with complex nitrogen sources such as casein hydrolysates or yeast extracts, etc.) in the culture medium so low that the cells are considered deprived of the phosphate ions, leading to a reversible increase in the rate of protein degradation, an inhibition of RNA synthesis, a decrease in cell growth, and a decrease in ATP. This is described further in St. John and Goldberg, *J. Bacteriol.*, 143: 1223–1233 (1980). This starvation level is to be distinguished from the level of phosphate required for induction/repression of the phoA promoter. Complete starvation is not required to induce this promoter. pstS is thought to be the cells' sensor of phosphate levels and therefore indirectly induces phoA expression. The desired inorganic phosphate concentration for inducing polypeptide production will depend on such factors as the type of polypeptide being produced, the type of host cell, the type of medium, and the culture conditions employed. An exemplary concentration for this purpose is 0.1–10 μmolar.

The technique of "polymerase chain reaction," or "PCR," as used herein generally refers to a procedure wherein minute amounts of a specific piece of nucleic acid, RNA, and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5'-terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, (Stockton Press, NY, 1989). For a recent review on PCR advances, see Erlich et al., *Science*, 252: 1643–1650 (1991).

As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

B. Modes for Carrying Out the Invention

In the process herein, expression of the dsbA or dsbC gene is induced just before (immediately prior to) heterologous gene expression. The heterologous polypeptide and DsbA or DsbC protein are both secreted into the periplasm or the heterologous polypeptide is secreted into the culture medium of the bacteria into which nucleic acid encoding these polypeptides has been introduced. Preferably, the polypeptide is recovered from the periplasm of the bacteria.

The dsbA or dsbC nucleic acid may be cDNA or genomic DNA from any bacterial source, and is generally the native sequence. It is suitably separately placed from the nucleic acid encoding the heterologous polypeptide if the nucleic acids are on the same vector, i.e., they are not linked. In addition, the nucleic acid encoding DsbA or DsbC and the nucleic acid encoding the heterologous polypeptide are under separate, differently inducible promoters so that induction of expression can occur in the required sequential order. The nucleic acid encoding the DsbA or DsbC and the nucleic acid encoding the heterologous polypeptide may be integrated into the host cell genome or contained on autonomously replicating plasmids.

If the DsbA or DsbC are native products of the host cell, and if the factors controlling expression of these native genes are understood, such factors can be manipulated to achieve over-expression of the dsbA or dsbC genes, e.g., by induction of transcription from the natural promoter using known inducer molecules, by mutation of the nucleic acids controlling or repressing expression of the gene product to produce a mutant strain that inductively over-expresses the gene product, by second site mutations which depress the synthesis or function of factors that normally repress the transcription of the gene product, and the like.

In one alternative, the bacteria comprises two separate vectors respectively containing the nucleic acid encoding the DsbA or DsbC protein and the nucleic acid encoding the heterologous polypeptide.

In another alternative, the nucleic acid encoding the DsbA or DsbC protein and the nucleic acid encoding the heterologous polypeptide are contained on the same vector but are under the control of separate inducible promoters and separate signal sequences.

The heterologous nucleic acid (e.g., cDNA or genomic DNA) is suitably inserted into a replicable vector for expression in the bacterium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes, and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli is typically transformed using pBR322, a plasmid derived from an E. coli species (see, e.g., Bolivar et al., Gene, 2: 95 [1977]). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, 1 pp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains an inducible promoter that is recognized by the host bacterial organism and is operably linked to the nucleic acid encoding the polypeptide of interest. It also contains a separate inducible promoter operably linked to the nucleic acid encoding the DsbA or DsbC protein. Inducible promoters suitable for use with bacterial hosts include the β-lactamase and lactose promoter systems (Chang et al., Nature, 275: 615 [1978]; Goeddel et al., Nature, 281: 544 [1979]), the arabinose promoter system (Guzman et al., J. Bacteriol., 174: 7716–7728 [1992]), alkaline phosphatase, a tryptophan (trp) promoter system (Goeddel, Nucleic Acids Res., 8: 4057 [1980] and EP 36,776) and hybrid promoters such as the tac promoter (deBoer et al., Proc. Natl. Acad. Sci. USA, 80: 21–25 [1983]). However, other known bacterial inducible promoters are suitable. Their nucleotide sequences have been published, thereby enabling a skilled worker operably to ligate them to DNA encoding the polypeptide of interest or to the dsbA or dsbC genes (Siebenlist et al., Cell, 20: 269 [1980]) using linkers or adaptors to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA. If the host contains a pstS variant gene, the expression vector for producing a heterologous polypeptide contains an alkaline phosphatase promoter that is recognized by the host bacterial organism and is operably linked to the nucleic acid encoding the polypeptide of interest. This promoter initiates increased levels of transcription from DNA under its control in response to a decreased concentration of inorganic phosphate in the culture medium. The phoA promoter can be removed from the bacterial source DNA by restriction enzyme digestion and inserted into the vector containing the desired DNA.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA*, 74: 5463–5467 (1977) or Messing et al., *Nucleic Acids Res.*, 9: 309 (1981) or by the method of Maxam et al., *Methods in Enzymology*, 65: 499 (1980).

Suitable bacteria for this purpose include archaebacteria and eubacteria, especially eubacteria, and most preferably Enterobacteriaceae. Examples of useful bacteria include Escherichia, Enterobacter, Azotobacter, Erwinia, Bacillus, Pseudomonas, Klebsiella, Proteus, Salmonella, Serratia, Shigella, Rhizobia, Vitreoscilla, and Paracoccus. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYC177, or pKN410 are used to supply the replicon.

*E. coli* strain W3110 is a preferred host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 1A2, which has the complete genotype tonAΔ (also known as ΔfhuA); *E. coli* W3110 strain 9E4, which has the complete genotype tonAΔ ptr3; *E. coli* W3110 strain 27C7 (ATCC 55,244), which has the complete genotype tonAΔ ptr3 phoAΔE15 Δ(argF-lac)169 ompTΔ degP41kan$^r$; *E. coli* W3110 strain 37D6, which has the complete genotype tonAΔ ptr3 phoAΔE15 Δ(argF-lac)169 ompTΔ degP41kan$^r$ rbs7Δ ilvG; *E. coli* W3110 strain 40B4, which is strain 37D6 with a non-kanamycin resistant degP deletion mutation; *E. coli* W3110 strain 33D3, which has the complete genotype tonA ptr3 lacIq LacL8 ompT degP kan$^r$; *E. coli* W3110 strain 36F8, which has the complete genotype tonA phoA Δ(argF-lac) ptr3 degP kan$^R$ ilvG+, and is temperature resistant at 37° C.; and an *E. coli* strain having the mutant periplasmic protease(s) disclosed in U.S. Pat. No. 4,946,783 issued Aug. 7, 1990.

Preferably, the host in nature contains a native psts gene. For the method herein that native gene is lacking and is replaced by the psts variant gene, which is preerably homologous to the native psts gene normally present in the host cells. Suitable bacteria for this purpose include eubacteria, especially Enterobacteriaceae, where the psts gene is thus far found. Examples of bacteria belonging to Enterobacteriaceae include Escherichia, Enterobacter, Erwinia, Klebsiella, Proteus, Salmonella, Serratia, and Shigella. One preferred *E. coli* host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYA177, or pKN410 are used to supply the replicon. *E. coli* strain W3110 is a particularly preferred parent host because it is a common host strain for recombinant DNA product fermentations. Preferably, the host cell should secrete minimal amounts of proteolytic enzymes. For example, strain W3110 may be modified to effect a genetic mutation in the genes encoding proteases, with examples of such hosts including *E. coli* W3110 strain 9E4, which has the complete genotype tonA ptr3, the preparation of which is described below, and *E. coli* W3110 strain 27C7, which has the complete genotype tonAΔptr3 phoAΔE15 Δ(argF-lac) 169 ompTΔdegP41kan$^r$. Strain 27C7 was deposited on 30 Oct. 1991 in the American Type Culture Collection as ATCC No. 55,244. Alternatively, the strain of *E. coli* having mutant periplasmic protease disclosed in U.S. Pat. No. 4,946,783 issued 7 Aug. 1990 may be employed.

Host cells are transfected, and preferably transformed with the above-described expression vectors of this invention and cultured in conventional nutrient media modified as appropriate for inducing the various promoters.

Transfection refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* [New York: Cold Spring Harbor Laboratory Press, 1989], is generally used for bacterial cells that contain substantial cell-wall barriers. Another method for transformation employs polyethylene glycol/DMSO, as described in Chung and Miller, *Nucleic Acids Res.*, 16: 3580 (1988). Yet another method is the use of the technique termed electroporation.

For purposes of this invention, a PstS variant contains one or more amino acid mutations within its phosphate-binding region, and is preferably from *E. coli*. Such variants may be prepared by any means, e.g., recombinant, synthetic, or partially synthetic. Amino acid sequence variants of PstS are suitably prepared by introducing appropriate nucleotide changes into the pstS DNA. Such variants include, for example, deletions from, or insertions or substitutions of, residues within the amino acid sequence shown for *E. coli* PstS in FIG. 1 of U.S. Pat. No. 5,304,472. Any combination of deletion, insertion, and substitution is made to arrive at the final construct, provided that the final construct possesses the desired characteristics. The variants and their method of construction are described more fully in U.S. Pat., No. 5,304,472, the disclosure of which is incorporated by reference.

For the design of amino acid sequence variants of PstS, the preferred induction characteristics will depend on the location of the mutation site within the phosphate-binding region and the nature of the mutation. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

While the site for introducing an amino acid sequence variation is predetermined, the nature of the mutation per se need not be predetermined. For example, to maximize the performance of a mutation at a given site, random mutagenesis is suitably conducted at the target codon or region and the expressed PstS variants are screened for the most favorable induction characteristics.

Amino acid sequence deletions within the phosphate-binding domain of PstS generally will range from about 1 to 5 residues, and typically are contiguous. Contiguous deletions ordinarily are made in even numbers of residues, but single or odd numbers of deletions are within the scope hereof.

Amino acid sequence insertions are intrasequence insertions of single or multiple amino acid residues within the phosphate-binding domain, generally ranging from about 1 to 5 residues, most preferably 1 to 3. Insertions are preferably made in even numbers of residues, but this is not required.

A third group of variants, which are preferred herein, are amino acid substitution variants. These variants have at least one amino acid residue within the phosphate-binding region of the native PstS molecule removed and a different residue inserted in its place.

Substantial modifications in phosphate-binding ability of the PstS protein are accomplished by selecting substitutions that differ significantly in their effect on maintaining (a) the structure of the PstS polypeptide backbone in the area of the substitution, for example, as a sheet or helical conformation, (b) the charge or hydrophobicity of the molecule at the target site, or (c) the bulk of the side-chain. Naturally occurring residues are divided into groups based on common side-chain properties:

(1) hydrophobic: norleucine, cys, met, ala, val, leu, tyr, phe, trp, ile;
(2) neutral hydrophilic: ser, thr;
(3) acidic: asp, glu;
(4) basic: asn, gln, his, lys, arg; and
(5) residues that influence chain orientation: gly, pro.

Preferably, the variants herein are those in which one or more of the amino acid residues positioned at the critical phosphate-binding region of the native counterpart protein is replaced with one or more different amino acids. For *E. coli* pstS variants, preferably residues thr, pro, or leu are substituted for the serine residue at position 139, residue his is substituted for the threonine residue at position 141, residues phe, leu, met, tyr, ala, cys, or gly are substituted for the threonine residue at position 10, and/or residues val, ala, leu, or ser are substituted for the asparagine residue at position 56 of native PstS. The most preferred *E. coli* PstS variants herein are those wherein a hydrophobic amino acid is substituted for the threonine residue at position 10, most preferably T10M PstS and T10Y PstS, and the variants D56S PstS and T141H PstS, using the nomenclature indicated below. Such amino acid changes may also be combined to provide a variant molecule with more than one altered amino acid.

Nucleic acid molecules encoding amino acid sequence variants of PstS are prepared by a variety of methods known in the art. These methods include, but are not limited to, preparation by oligonucleotide-mediated (or site-directed) mutagenesis, alanine-scanning mutagenesis, random mutagenesis, PCR mutagenesis, and cassette mutagenesis of an earlier prepared variant or a non-variant version of PstS.

Oligonucleotide-mediated mutagenesis represents a preferred method for preparing substitution, deletion, and insertion variants of the psts gene, although other methods may be utilized as desired. This technique is well known in the art as described by Zoller and Smith, *Nucleic Acids Res.*, 10: 6487 (1982). Briefly, pstS DNA is altered by hybridizing an oligonucleotide encoding the desired mutation to a DNA template, where the template is the single-stranded form of a plasmid or bacteriophage containing the unaltered or native DNA sequence of pstS. After hybridization, a DNA polymerase is used to synthesize an entire second complementary strand of the template that will thus incorporate the oligonucleotide primer, and will code for the selected alteration in the pstS DNA.

Generally, oligonucleotides of at least 25 nucleotides in length are used. A preferred oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153: 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, NY 1989).

Alternatively, a single-stranded DNA template may be generated by denaturing double-stranded plasmid (or other) DNA using standard techniques.

A useful method for identification of certain residues or regions of the PstS protein that are preferred locations for mutagenesis is called "alanine-scanning mutagenesis," as described by Cunningham and Wells, *Science*, 244: 1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the expressed PstS variants are screened for the most preferred combination of desired activity.

For alteration of the native DNA sequence (to generate amino acid sequence variants, for example), the preferred method is the combination of oligonucleotide-directed mutagenesis and random mutagenesis as described by Kunkel et al., *Methods Enzymol.*, 154: 367 (1987). In this method, oligonucleotide-directed mutagenesis is employed to randomize particular codons of the wild-type pstS gene to encode all possible residues. A pool of oligonucleotides with complementary sequence (about 10–15 bases) flanking the codon of choice is used. The codon of choice is replaced with the nucleotides NNS, where N is any nucleotide and S is G or C, to give a pool of oligonucleotides encoding all possible amino acids in 32 codons.

In this preferred method, a pBR322-derived plasmid with a single-stranded origin of replication is prepared as a single-stranded plasmid template in an *E. coli* dut- ung- strain such as CJ236 (Kunkel et al., supra) . These two mutations in the strain cause the incorporation of one or more uracil nucleotides into the single-stranded DNA instead of thymine. The random oligonucleotides are annealed, filled in with *E. coli* phage T7 DNA polymerase, ligated, and transformed into a wild-type strain of *E. coli* such as W3110 or strain 13G8 (W3110 tonAΔ PhoS64). The latter strain is pstS minus and derived from CGSC6777 (C75-b), which is derived from C75, described by Amemura et al., *J. Bacter.*, 152: 692–701 (1982). The wild-type strain corrects the uracil misincorporation using the synthetic mutant strand as a template so as to produce about 90% mutants.

DNA encoding PstS mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of PstS. While the following discussion refers to DNA, it is understood that the technique also finds application with RNA. The PCR technique generally refers to the following procedure (see Erlich, supra, the chapter by R. Higuchi, p. 61–70):When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 µg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 µl. The reaction mixture is overlayed with 35 µl mineral oil. The reaction mixture is denatured for five minutes at 100° C., placed briefly on ice, and then 1 µl *Thermus aquaticus* (Taq) DNA polymerase (5 units/µl, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.

30 sec. 72° C., then 19 cycles of the following:

30 sec. 94° C.

30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene*, 34: 315 (1985). The starting material is the plasmid (or other vector) comprising the pstS DNA to be mutated. The codon(s) in the pstS DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the pstS DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated pstS DNA sequence.

Nucleic acid encoding the PstS variant may also be chemically synthesized and assembled by any of a number of techniques, prior to expression in a host cell. [See, e.g., Caruthers, U.S. Pat. No. 4,500,707; Balland et al., *Biochimie*, 67: 725–736 (1985); Edge et al., *Nature*, 292: 756–762 (1982)].

For purposes of shorthand designation of the PstS variants described herein, it is noted that numbers refer to the amino acid residue/position along the amino acid sequences of the mature PstS protein. Amino acid identification uses the single-letter alphabet of amino acids, i.e.,

| Asp | D | Aspartic acid | Ile | I | Isoleucine |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

The designation for a substitution variant herein consists of a letter followed by a number followed by a letter. The first (leftmost) letter designates the amino acid in the wild-type, mature PstS protein. The number refers to the amino acid position where the amino acid substitution is being made, and the second (right-hand) letter designates the amino acid that is used to replace the wild-type amino acid. The designation for an insertion variant consists of the letter i followed by a number designating the position of the residue in wild-type, mature PstS protein before which the insertion starts, followed by one or more capital letters indicating, inclusively, the insertion to be made. The designation for a deletion variant consists of the letter d followed by the number of the start position of the deletion to the number of the end position of the deletion, with the positions being based on the wild-type, mature PstS protein. Multiple mutations are separated by a comma in the notation for ease of reading them.

Examples of the nomenclature for *E. coli* PstS protein are as follows: a substitution variant where the threonine at position 10 of the wild-type PstS protein is replaced with a methionine residue is designated T10M PstS. A substitution variant with multiple substitutions M and S at positions 10 and 56 of the wild-type PstS protein is designated T10M, D56S PstS. An insertion variant where cysteine and valine are inserted after the threonine at position 10 of wild-type PstS is designated iT10CV PstS. A deletion variant where the amino acid (threonine) at position 10 is deleted from the wild-type, mature PstS is designated dT10 PstS. As indicated in the above examples, the notation 'PstS' follows after each mutant.

Most deletions and insertions, and substitutions in particular, are not expected to produce radical changes in the characteristics of the PstS molecule. However, when it is difficult to predict the exact effect of the substitution, deletion, or insertion in advance of doing so, one skilled in the art appreciates that the effect may be evaluated by routine screening assays.

A DNA variant typically may be made by random and/or site-specific mutagenesis of the native PstS-encoding nucleic acid and transfection or integration of the psts variant gene into the chromosomes of a bacterial host, or by random mutagenesis of a host containing the native pstS gene. The nucleic acid variant may then be screened in a suitable screening assay for the desired characteristic.

For example, in one embodiment, the mutant genes are screened for alkaline phosphatase activity in high phosphate (about 3 mM phosphate) by transforming the mutant pool into a pstS− W3110 strain such as strain 13G8 described above or C75 (Amemura et al., supra) and plating on LB-BCIP-carbenicillin plates. Plasmids are isolated from blue colonies and the psts gene is then sequenced to determine specific mutations.

Alternatively, single transformants are grown overnight in duplicate 96-well plates containing either high (2–5 mM) or low (0.3 mM) phosphate. Then aliquots are assayed for PhoA activity by PNPP hydrolysis. Mutants with increased activity, particular those with higher activity in high phosphate concentration, are sequenced and further characterized for activity.

Sequenced mutants selected from either screen are further characterized by growing cells in 96-well plates containing a range of phosphate concentrations from 0.02 to 50 mM and assaying aliquots for PhoA activity. The mutants selected from this screening are integrated into the chromosomal psts locus to replace the wild-type gene and to be under the transcriptional control of the wild-type PstS promoter. The integrated strains are characterized by assaying PhoA levels.

Those strains meeting this last test can then be evaluated in shake-flask cultures with varying initial phosphate concentrations to assay for the expression of either homologous or heterologous protein products as appropriate. In addition or alternatively, the new organisms can be evaluated in high-cell-density fermentations where different phosphate feeding rates are employed after the initially charged phosphate is depleted. As a final test and optimization, these strains can then be used in a fermentor where phosphate levels can be monitored and regulated on-line. The cells are transformed with the nucleic acid encoding this polypeptide and the cells will be assayed for levels of that polypeptide produced under transcriptional control of the specific promoter employed, e.g., the phoA promoter.

In the latter application where the phoA promoter is used, the phosphate level of the medium in which the altered bacterial host cells are cultured is measured on line (i.e., by continuous sampling), starting with an excess of phosphate (40 mM) in the medium. Then the phosphate level is depleted to about 0.2 to 5 mM phosphate, and the rate of induction of the PhoA promoter is measured by techniques known to those skilled in the art. The preferred PstS mutants are those wherein the polypeptide induction at this concentration of phosphate increases the ultimate yield of polypeptide or increases the relative amount of intact polypeptide or the cell density.

If the nucleic acid encoding the PstS variant is produced outside the bacterial host cell that will ultimately produce the polypeptide of interest, the nucleic acid is introduced into the appropriate bacterial cell using any suitable method, including transfection and transformation by a vector encoding the PstS variant and, preferably, integration into the chromosome of the bacterial cells by any suitable method known in the art. An example of insertion of the pstS gene into the host genome includes that using the E. coli species as host. In this case included in the vector for transformation is a DNA sequence that is complementary to a sequence found in E. coli genomic DNA. Transfection of E. coli with this vector results in homologous recombination with the genome and insertion of the pstS variant gene. The host for this purpose is either psts minus or has its wild-type pstS gene replaced by the pstS variant gene upon integration thereof.

Bacterial cells used to produce the polypeptide of interest of this invention are cultured in suitable media in which the alkaline phosphatase promoter can be partially or completely induced as described generally, e.g., in Sambrook et al., supra. The culturing need never take place in the absence of inorganic phosphate or at phosphate starvation levels. At first, the medium contains inorganic phosphate in an amount above the level of induction of protein synthesis and sufficient for the growth of the bacterium. As the cells grow and utilize phosphate, they decrease the level of phosphate in the medium, thereby causing induction of synthesis of the polypeptide.

Any other necessary supplements besides carbon, nitrogen, and inorganic phosphate sources may also be included at appropriate concentrations introduced alone or as a mixture with another supplement or medium such as a complex nitrogen source. The pH of the medium may be any pH from about 5–9, depending mainly on the host organism. Preferably, the medium contains no reduced glutathione, and the bacteria are not cultured so as to over-express nucleic acid encoding the heat-shock transcription factor, RpoH.

For induction, typically the cells are cultured until a certain optical density is achieved, e.g., a $A_{550}$ of about 60–80, at which point induction is initiated (e.g., by addition of an inducer, by depletion of a medium component, etc.), to induce expression of the dsbA or dsbC gene. When the optical density reaches a higher amount, e.g., a $A_{550}$ of about 80–100, induction of the alkaline phosphatase promoter for the heterologous polypeptide is effected.

Gene expression may be measured in a sample directly, for example, by conventional northern blotting to quantitate the transcription of mRNA. Thomas, Proc. Natl. Acad. Sci. USA, 77: 5201–5205 (1980). Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

Procedures for observing whether an expressed or over-expressed gene product is secreted are readily available to the skilled practitioner. Once the culture medium is separated from the host cells, for example, by centrifugation or filtration, the gene product can then be detected in the cell-free culture medium by taking advantage of known properties characteristic of the gene product. Such properties can include the distinct immunological, enzymatic, or physical properties of the gene product.

For example, if an over-expressed gene product has a unique enzyme activity, an assay for that activity can be performed on the culture medium used by the host cells. Moreover, when antibodies reactive against a given gene product are available, such antibodies can be used to detect the gene product in any known immunological assay (e.g., as in Harlowe et al., Antibodies: A Laboratory Manual, Cold Spring Harbor Laboratory Press, New York, 1988).

The secreted gene product can also be detected using tests that distinguish polypeptides on the basis of characteristic physical properties such as molecular weight. To detect the physical properties of the gene product, all polypeptides newly synthesized by the host cell can be labeled, e.g., with a radioisotope. Common radioisotopes that can be used to label polypeptides synthesized within a host cell include tritium ($^3H$), carbon-14 ($^{14}C$), sulfur-35 ($^{35}S$), and the like. For example, the host cell can be grown in $^{35}S$-methionine or $^{35}S$-cysteine medium, and a significant amount of the 35S label will be preferentially incorporated into any newly synthesized polypeptide, including the over-expressed heterologous polypeptide. The $^{35}S$-containing culture medium is then removed and the cells are washed and placed in fresh non-radioactive culture medium. After the cells are maintained in the fresh medium for a time and under conditions sufficient to allow secretion of the $^{35}S$-radiolabeled expressed heterologous polypeptide, the culture medium is collected and separated from the host cells. The molecular weight of the secreted, labeled polypeptide in the culture medium can then be determined by known procedures, e.g., polyacrylamide gel electrophoresis. Such procedures, and/or other procedures for detecting secreted gene products, are provided in Goeddel, D. V. (ed.) 1990, Gene Expression Technology, Methods in Enzymology, Vol. 185 (Academic Press), and Sambrook et al., supra.

For secretion of an expressed or over-expressed gene product, the host cell is cultured under conditions sufficient for secretion of the gene product. Such conditions include, e.g., temperature, nutrient, and cell density conditions that permit secretion by the cell. Moreover, such conditions are those under which the cell can perform basic cellular functions of transcription, translation, and passage of proteins from one cellular compartment to another, as are known to those skilled in the art.

The polypeptide of interest is recovered from the periplasm or culture medium as a secreted polypeptide. It is often preferred to purify the polypeptide of interest from recombinant cell proteins or polypeptides and from the DsbA or DsbC protein to obtain preparations that are substantially homogeneous as to the polypeptide of interest. As a first step, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane bound, is soluble, or is present in an aggregated form. The polypeptide thereafter is solubilized and refolded, if necessary, and is purified from contaminant soluble proteins and polypeptides. In a preferred embodiment, the aggregated polypeptide is isolated, followed by a simultaneous solubilization and refolding step, as disclosed in U.S. Pat. No. 5,288,931.

Another preferred method for isolating exogenous polypeptides from a complex biological mixture containing polypeptides and non-polypeptides contained in a fermentation broth, such as the one described above, involves contact of reagents with the cells, preferably the cell culture, containing the polypeptide in a non-native conformation, so that an aqueous extraction/isolation can take place. Preferably, the method entails direct addition of reagents to the fermentation vessel after the polypeptide has been produced recombinantly, thereby avoiding extra steps of harvesting, homogenization, and centrifugation to obtain the polypeptide. While the remaining particulates can be removed by Gaulin homogenization and resuspension, suspension, filtration, or a combination thereof, this method utilizes a multiple-phase extraction system for purifying recombinant polypeptides from the remaining particulates.

In particular, this method is preferred for non-native mammalian polypeptides produced recombinantly in bacterial cells, including *E. coli*, which form refractile bodies in the periplasm of the cells. In this system, one or more denaturants (chaotropic agent), such as urea, guanidine hydrochloride, and/or a base, and a reducing agent, such as dithiothreitol or cysteine, are added to the polypeptide-containing medium and then phase-forming species are added to the broth. Once this second group of reagents is added to the broth, multiple phases are formed whereby one phase is enriched in the polypeptide and depleted in biomass solids and nucleic acids. Preferably, the system has two to four phases, and more preferably two phases, one being enriched in polypeptide and the other being enriched in biomass solids and nucleic acids. Preferably, the desired polypeptide partitions to the upper phase so that the upper phase is enriched in the polypeptide and depleted in the biomass solids and nucleic acids.

Specifically, after fermentation is complete, the cell culture is contacted with one or more chaotropic agents, an optional reducing agent, and phase-forming reagents so that multiple phases are formed, one phase of which is enriched in the polypeptide of interest. It is preferred to add the chaotrope and reducing agent first to extract the polypeptide from the cell and maintain its solubility in the broth before the phase-forming reagents are added. Also, while the polypeptide of interest can be extracted from (and enriched in) any phase, preferably it is recovered from the uppermost phase.

Most preferably, the chaotropic agent and optional reducing agent are added directly to the fermentation broth in the fermentation vessel before isolation of the polypeptide so that the reagents permeate the cells and the polypeptide is solubilized and diffuses to the surrounding medium. The reducing agent is added if the polypeptide contains at least one sulfhydryl group.

Examples of suitable reducing agents include dithiothreitol (DTT), β-mercaptoethanol (BME), cysteine, thioglycolate, and sodium borohydride. The amount of reducing agent to be present in the buffer will depend mainly on the type of reducing agent and chaotropic agent, the type and pH of the buffer employed, and the type and concentration of the polypeptide in the buffer. An effective amount of reducing agent is that which is sufficient to eliminate intermolecular disulfide-mediated aggregation. For example, with 0.5–6 mg/mL IGF-I in a buffered solution at pH 7.5–10.5 containing 1–4M urea, the DTT concentration is at about 1–20 mM, and the concentration of cysteine is at about 10–50 mM. The preferred reducing agent is DTT at about 2–10 mM or cysteine at about 30–50 mM.

Chaotropic agents suitable for practicing this method of extraction include, e.g., urea and salts of guanidine or thiocyanate, more preferably urea, guanidine hydrochloride, or sodium thiocyanate. The amount of chaotropic agent necessary to be present in the buffer depends, for example, on the type of chaotropic agent and polypeptide present. The amount of chaotropic agent to be added to the fermentation broth will be sufficiently high to extract the polypeptide from the cell and maintain its solubility in the broth. If the polypeptide is to be extracted from the top phase, the amount of chaotropic agent must be sufficiently low so that after addition of the phase-forming species, the density is not increased to a point where the solids rise to the top instead of settling to the bottom. Generally the concentration of chaotropic agent is about 0.1 to 9M, preferably about 0.5–9M, more preferably about 0.5 to 6M, and most preferably about 0.5–3M. Also, preferably the chaotropic agent is added to the culture medium before the phase-forming reagents are added. The preferred chaotropic agent herein is urea at about 1.5–2.5M, more preferably at about 2M, or guanidine hydrochloride at about 0.5–3M. Most preferably, the chaotropic agent is urea.

The concentration of the polypeptide in the aqueous solution to which the chaotrope and reducing agent are added must be such that the polypeptide will be recovered in the maximum yield. The exact amount to employ will depend, e.g., on the type of polypeptide and the concentrations and types of other ingredients in the aqueous solution, particularly the reducing agent, chaotropic agent, phase-forming species, and pH. For polypeptides in general, the preferred concentration of polypeptide is about 0.1 to 15 mg/mL. The preferred concentration of IGF-I (resulting in the maximum yield of denatured or non-native IGF-I) is in the range of 0.5–6 mg per mL, more preferably 1.5–5 mg/mL.

The types of phase-forming species to employ herein depend on many factors, including the type of polypeptide and the ingredients in the fermentation broth being treated. The species must be selected so that the polypeptide does not precipitate and one phase is more hydrophobic than the other phase so that the polypeptide will be located in the more hydrophobic phase and the biomass solids and nucleic acids will settle to the less hydrophobic phase.

The phase-forming species may be a combination of agents, including polymer combinations (polymer-polymer), polymer-salt combinations, solvent-salt, and polymer-solvent combinations. Suitable polymers are both highly hydrophilic polymers and less hydrophilic polymers, i.e., any phase-forming polymers that are known in the art. Examples include polyethylene glycol or derivatives thereof, including various molecular weights of PEG such as PEG 4000, PEG 6000, and PEG 8000, derivatives of PEG described, for example, in Grunfeld et al., *Appl. Biochem. Biotechnol.*, 33: 117–138 (1992), polyvinylpyrrolidone (PVP), in a preferable molecular weight range of about 36,000 to 360,000, starches such as dextran (e.g., dextran 70 and 500), dextrins, and maltodextrins (preferable molecular weight between about 600 and 5,000), sucrose, and Ficoll-400™ polymer (a copolymer of sucrose and epichlorohydrin). The preferred polymer herein is polyethylene glycol, polypropylene glycol, polyvinylpyrrolidone, or a polysaccharide such as a dextran. The most preferred polymer herein is PEG of different molecular weights or a PEG-polypropylene glycol combination or copolymer.

Examples of suitable organic solvents include ethylene glycol, glycerol, dimethyl sulfoxide, polyvinylalcohol, dimethylformamide, dioxane, and alcohols such as methanol, ethanol, and 2-propanol. Such solvents are such that, when added to aqueous solution, they increase the hydrophobicity of the solution.

The salts can be inorganic or organic and preferably do not act to precipitate the polypeptide. Salts containing transition elements are not preferred as they tend to precipitate the polypeptide. Anions are selected that have the potential for forming aqueous multiple-phase systems. Examples include ammonium sulfate, sodium dibasic phosphate, sodium sulfate, ammonium phosphate, potassium citrate, magnesium phosphate, sodium phosphate, calcium phosphate, potassium phosphate, potassium sulfate, magnesium sulfate, calcium sulfate, sodium citrate, manganese sulfate, manganese phosphate, etc. Types of salts that are useful in forming bi-phasic aqueous systems are evaluated more fully in Zaslavskii et al., *J. Chrom.*, 439: 267–281 (1988). Preferred salts herein are sulfates, phosphates, or citrates and are alkali or alkaline earth metals. More preferred are sulfates and citrates, and most preferred are sulfates since there are fewer pH limitations with sulfates. The most preferred salts herein are sodium sulfate and sodium citrate.

The amounts of phase-forming species to add to the polypeptide of interest to obtain a satisfactory multiple-phase system are those known in the art. The amount of phase-forming species added to the polypeptide will depend on such factors as, for example, the amount of chaotropic agent and reducing agent, if any, already present in the fermentation broth, the nature of the cell culture media, the type of cells used in the fermentation, the type of polypeptide being treated, whether the polypeptide will be recovered from the lower or upper phase, and the type(s) of phase-forming species being added. The general concentration of polymer employed is about 5% (w/w) up to the limit of solubility for the polymer and the concentration of salt employed is about 3% (w/w) up to the limit of solubility for the salt, depending on the size of the phase-volume ratio needed. The phase-volume ratio must be sufficient to accommodate the biomass solids. The types and amounts of phase-forming species that are effective can be determined by phase diagrams and by evaluating the final result, i.e., the degree of purity and the yield of the polypeptide of interest. If the phase-forming species are a polymer-salt combination, preferably the concentration of salt added is about 4–15% (w/w) and the concentration of polymer is 5–18% (w/w) so that the desired polypeptide will be in an opposite phase from that in which the biomass solids and nucleic acids are present.

If the system desired is one where the polypeptide is distributed in the top phase and the biomass solids and nucleic acids are in the bottom phase, then there is a window of concentrations of phase-forming species. When higher amounts of chaotropic agent are added to maintain solubilization, the higher the amount of phase-forming species required. However, a high concentration of all these reagents will increase the density of the solution. A high density will cause the biomass solids to settle less readily. An overly high density will cause biomass solids to float on the surface. Hence, the concentrations of chaotropic agent and phase-forming species must be sufficiently high to maintain a fully solubilized polypeptide, but low enough to allow the biomass solids to sediment to the opposite (lower) phase.

If the polypeptide is to be recovered in the upper phase, typically the salt concentration will be about 4–7% (w/w) and the polymer concentration will be about 12–18% (w/w), depending, e.g., on the type of salt, polymer, and polypeptide. If an organic solvent is added as a phase-forming species, such as ethanol, it is preferably added in a concentration of about 10 to 30% (volume/volume) of the solution, depending, e.g., on the type of polypeptide and alcohol and if any other phase-forming species is present, preferably at a concentration of about 20% (v/v).

The exact conditions for contacting the cell culture with the various reagents will depend on, e.g., the pH of the buffer, the types of phase-forming reagents, and the types and concentrations of polypeptide and chaotropic and reducing agents. The reaction temperature is generally about 20°–40° C., more preferably room temperature. The contacting step will generally be carried out for at least about 30 minutes, preferably about 30 minutes to 12 hours depending on whether side-reactions will occur, more preferably about 30 minutes to 8 hours, and most preferably about 30 minutes to 1.5 hours.

If the polypeptide is being unfolded, the degree of unfolding is suitably determined by chromatography of the non-native polypeptide, including hydrophobic interaction chromatography or ion-exchange chromatography. Increasing peak area for the non-native material indicates how much non-native polypeptide is present.

Once the multiple-phase system is established, one phase will be enriched in the polypeptide and depleted in the disrupted particles and cells comprising the biomass solids and nucleic acids. In a two-phase system, preferably the top phase is enriched in the polypeptide whereas the bottom phase is enriched in the disrupted particles and cells. The polypeptide can be easily recovered by separation of the phases. This recovery step may be accomplished by decanting the upper phase, by draining the lower phase, or by centrifugation. The polypeptide can then be isolated from the phase in which it is contained by changing the pH of the phase so as to precipitate the polypeptide or by adding a suitable solvent, whereupon the precipitated polypeptide is suitably recovered by centrifugation or filtration or as a slurry.

Alternatively, the polypeptide can be recovered from the polymer-containing phase by re-extraction by addition of a suitable polymer, salt, or solvent. In the case of IGF-I, the polypeptide is recovered from the isolated polymer phase by lowering the pH so that the IGF-I will precipitate, resulting in a yield of IGF-I of as much as or more than about 97%. The DsbA or DsbC protein would be separated from the polypeptide at this stage.

Once obtained from the liquid phase of the multiple-phase system, or at a later stage of purification, the polypeptide is suitably refolded into an active conformation. One suitable refolding method that can be utilized is that which follows.

After the polypeptide is solubilized and extracted by the multiple-phase extraction system herein, it is placed or diluted into a buffer containing solvent, chaotropic agent, salt, and a minimal amount of a copper or manganese salt. This buffer unexpectedly increases refolding yields of polypeptide from any type of host. This buffer is at a pH of about 7 to 12, depending mainly on the type of polypeptide and reducing agent, preferably about 8 to 11, more preferably pH 8.5 to 11, and most preferably 8.5 to 10.5.

One key ingredient of the buffer is an alcoholic or polar aprotic solvent at a concentration of about 5–40% (v/v), preferably 10 to 30% (volume/volume) of the solution, depending, e.g., on the type of polypeptide and solvent, and the concentration of chaotropic agent. It is most preferably at a concentration of about 20% (v/v).

A second key ingredient to this buffer is an alkaline earth, alkali metal, or ammonium salt, which is present in a concentration of about 0.2 to 3M, preferably 0.2 to 2M, depending mainly on the chaotrope concentration, solvent concentration, and the type of alkaline earth, alkali metal, or ammonium salt and polypeptide employed. For example, if the cation is sodium, potassium, or ammonium, the concentration is about 0.5 to 3M, but if the cation is magnesium, the concentration is about 0.2 to 1M.

A third key ingredient of the buffer is an effective amount of a chaotropic agent. The amount of such chaotrope will depend mainly on the concentration of alkaline earth, alkali metal, or ammonium salt, the concentration of solvent, the specific type of alkaline earth, alkali metal, or ammonium salt employed, the specific type of chaotropic agent employed, and the type of polypeptide, as well as the pH of the buffer, but in general will range from about 0.1 to 9M, preferably about 0.5 to 6M, and most preferably about 1.5 to 4M. As to specific chaotropes, preferably about 0.1 to 2M of guanidine hydrochloride, and preferably about 1–3M, more preferably about 1–2.5M, and most preferably about 2M, of urea is utilized.

A fourth key ingredient of the buffer is an effective amount of a transition metal salt selected from copper and manganese salts so that oxidation and resultant refolding will occur. The amount of copper or manganese salt depends mainly on the type of transition metal and polypeptide employed and the oxygen level present. The lower the rate of oxygen addition or the oxygen level, the higher the amount of copper or manganese salt that can be employed. The copper or manganese salt concentration is typically about 0.01 to 15 µM, preferably about 0.01 to 10 µM, more preferably about 0.01 to 5 µM, and even more preferably about 0.01 to 0.5 µM. The above preferred ranges are particularly preferred for IGF-I. If the concentration is increased beyond about 15 µM, unexpectedly the yield of correctly folded polypeptide decreases dramatically. Most preferably, the concentration of a copper or manganese salt is about 0.5 µM. The transition metal salt may already be present in the buffer without addition of exogenous transition metal salt, for example, if it is residual from the fermentation, or it may be added to the buffer, or both.

The buffer can be any of those listed above for the first buffered solution, with CAPSO, glycine, and CAPS being preferred at pH 8.5–11, particularly at a concentration of about 20 mM, and most preferably CAPSO and glycine. The polypeptide may be diluted with the refolding buffer, preferably at least five fold, more preferably at least about ten fold. Alternatively, the polypeptide may be dialyzed against the refolding buffer. The refolding is typically carried out at about 0°–45° C., preferably about 20°–40° C., more preferably about 23°–37° C., even more preferably about 25°–37° C., and most preferably about 25° C. for at least about one hour. The preferred temperature is not apparently affected by salt, solvent, and chaotropic agent levels, but may be affected by the presence of sucrose and glycerol, in which case it should be kept above about 20° C. The solution optionally also contains a reducing agent and an osmolyte.

The reducing agent is suitably selected from those described above for the solubilizing step in the concentration range given. Its concentration will depend especially on the concentrations of alkaline earth, alkali metal, or ammonium salt, polypeptide, and solvent. Preferably, the concentration of reducing agent is about 0.5 to 8 mM, more preferably about 1–5 mM, even more preferably about 0.5–2 mM. The preferred reducing agents are DTT and cysteine.

The optional osmolyte is preferably sucrose (in a concentration of about 0.25–1M) or glycerol (in a concentration of about 1–4M). More preferably, the sucrose concentration is at about 1M and the glycerol concentration is at about 4M.

The initial concentration of polypeptide in the folding buffer is such that the ratio of correctly folded to misfolded conformer recovered will be maximized, as determined by HPLC, RIA, or bioassay. The exact concentration will depend, for example, on the type of polypeptide employed. The preferred concentration of polypeptide (resulting in the maximum yield of correctly folded conformer) is in the range of about 0.1 to 15 mg/mL, more preferably about 0.1 to 6 mg/mL, and most preferably about 0.2 to 5 mg/mL.

In addition, a source of oxygen such as air or oxygen gas is entrained in or otherwise introduced into the buffer so as to effect oxidation together with the copper or manganese salt. The oxygen can be present in the buffer at any point in time, including before the polypeptide or any other reagents are added to the buffer.

The amount of oxygen source introduced will depend, e.g., on the type of vessel utilized, the type and concentration of polypeptide, the type of oxygen source, the type and amount of copper or manganese salt, and the type and amount of reducing agent present, if any, and the type and amount of chaotropic agent present as well as the pH of the buffer. Generally, the oxygen source will be introduced by passive means (e.g., as air in head space in a ratio of air space to fluid volume of 2:1) using an agitator. Alternatively, the oxygen source may be introduced by bubbling through a sparger. The rate of introduction of the oxygen must be sufficient to allow folding to reach completion in preferably about 1 to 12 hours, more preferably about 1 to 6 hours, and most preferably about 1 to 3 hours. The addition of molar oxygen is proportional to the reductant concentration and polypeptide concentration, but inversely proportional to the copper or magnesium salt concentration. The rate of oxidation is limited by the level of catalyst, not by the oxygen addition rate. A higher sparging rate is required for larger volume folding.

The degree of refolding that occurs upon this second incubation is suitably determined by the RIA titer of the polypeptide or by HPLC analysis using e.g., a Vydac or Baker C-18 column, with increasing RIA titer or correctly folded polypeptide peak size directly correlating with increasing amounts of correct, biologically active polypeptide conformer present in the buffer. The incubation is carried out to maximize the yield of correctly folded polypeptide conformer and the ratio of correctly folded polypeptide conformer to misfolded polypeptide conformer recovered, as determined by RIA or HPLC, and to minimize the yield of multimeric, associated polypeptide as determined by mass balance.

The following procedures are exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; and gel filtration using, for example, Sephadex G-75.

The following examples are offered by way of illustration and not by way of limitation. The disclosures of all patent and scientific references cited in the specification are expressly incorporated herein by reference.

EXAMPLE I

The dsbA nucleotide sequence was amplified using PCR techniques from p16-1 (Bardwell et al., supra, 1991) and a XbaI site was added at the 5' end and a ClaI site at the 3' end of the DsbA-encoding sequence. This DNA fragment was digested with the appropriate restriction enzymes and ligated with a 1.0-kb PstI-XbaI fragment of pKMTacII (deBoer et al., Proc. Natl. Acad. Sci. USA, 80: 21–25 [1983]) and a 3.6-kb ClaI-PstI fragment of pBKIGF-2B (U.S. Pat. No. 5,342,763). The resulting plasmid, pJJ41 (see FIG. 1), contains dsbA under the control of the tacII promoter and confers resistance to ampicillin and tetracycline. This plasmid was digested with ClaI and the ends were filled in by Klenow fragment and deoxynucleotides.

After inactivation of the Klenow fragment and extraction of the digested DNA, the DNA was subsequently digested with ScaI and the 1.5-kb fragment containing the 5' end of the β-lactamase gene and the TacII-dsbA element was purified. This was ligated with a 4.6-kb fragment of EcoRI-digested and filled-in pBKIGF-2B, which had also been digested with ScaI. This fragment of pBKIGF-2B contained the 3' end of the β-lactamase, allowing selection for resistance to ampicillin as well as the DNA sequences for resistance to tetracycline and production of IGF-I. This plasmid is denoted pJJ42 (see FIG. 1).

This plasmid was transformed into *E. coli* strain 33D3 (with the genotype W3110tonA ptr3 lacIq LacL8 ompT degP kan'). This strain was constructed in several steps using techniques involving transduction with phage P1kc, derived from P1 (J. Miller, *Experiments in Molecular Genetics*, Cold Spring Harbor, NY, Cold Spring Harbor Laboratory, 1972) and transposon genetics (Kleckner et al., *J. Mol. Biol.*, 116: 125–159 [1977]). The starting host used was *E. coli* K-12 W3110, which is a K-12 strain that is F- lambda- (Bachmann, *Bact. Rev.*, 36: 525–557 [1972]; Bachmann, "Derivations and Genotypes of Some Mutant Derivatives of *Escherichia coli* K-12," p. 1190–1219, in F. C. Neidhardt et al., ed., *Escherichia coli and Salmonella typhimurium: Cellular and Molecular Biology*, vol. 2, American Society for Microbiology, Washington, D.C., 1987).

Introduction of the tonA (fhuA) mutation and ptr3 mutation into the genome is described in detail in U.S. Pat. No. 5,304,472 issued Apr. 19, 1994. The resulting strain is designated 9E4. The lacI$^q$ (Muller Hill et al., *Proc. Natl. Acad. Sci. USA*, 59: 1259 [1968]) and lacL8 (Scaife and Beckwith, *Cold Spring Harbor Symp. Quant. Biol.*, 31: 403 [1967]) mutations were introduced into strain 9E4 by co-transduction with proC. First, a linked Tn5 insertion into proC and a phoAΔE15 (Sarthy, A. et al., *J. Bacteriol.*, 145: 288–292 [1981]) mutation were introduced. P1 transduction to proline prototrophy restored the proC gene and the phoA gene and also introduced the lacI$^q$lacL8 mutations. The lacI$^q$ mutation results in an overproduction of lac repressor compared to wild-type. The presence of the lacI$^q$ mutation can be observed on LB plates containing the chromogenic substrate 5-bromo-4-chloro-3-indolyl-β-D-galactoside (X-gal). On these plates a lacI$^+$ strain will be light blue, whereas a lacI$^q$ strain will be colorless. The LacL8 mutation is a promoter mutation that results in lower lac operon enzyme levels. The presence of the lacL8 mutation can be detected on MacConkey 1% lactose medium as colonies with a dark red center and beige surrounding edge.

Introduction of the ompT deletion and the degP mutation into the strain is described in detail in U.S. Pat. No. 5,304,472.

The final strain 33D3 is resistant to T1 and Ø80 phage, lacks three proteases, overproduces the lac repressor, and produces lower than wild type lac operon enzyme levels when induced. 33D3 cells containing pJJ42 were then grown in a 10-liter fermentor under conditions identical to IGF-I production as described in U.S. Pat. No. 5,304,472, Example II, 1×feed conditions. When the optical density ($A_{550}$) of the culture reached 60, IPTG or lactose was added in the amounts given below to induce the tacII promoter, thereby increasing dsbA expression. The growth medium was designed for phosphate depletion and phoA promoter induction to occur at an optical density ($A_{550}$) of 80 to 100. Total IGF-I production was measured by a high-pressure liquid chromatography (HPLC) assay described by U.S. Pat. No. 5,304,472.

The results are shown in Table 1 below:

TABLE 1

| Fermentation Run | Conditions | g/L IGF-I |
| --- | --- | --- |
| S1968 | pBKIGF-2B, no inducer | 3.0 |
| S1963 | pJJ42, 0.05 mM IPTG | 4.8 |
| S1964 | pJJ42, 1.0 mM IPTG | 4.8 |
| S1959 | pJJ42, 1.0% lactose | 4.0 |

The results show that over-expression of the dsbA gene in the periplasm of the bacteria improves the yield of IGF-I for all runs that were induced by either inducer. The increase in IGF-I accumulation was about 60%. The correctly folded IGF-I can be recovered in high yield by liquid-liquid extraction followed by aerobic refolding as described above or by methods described in U.S. Pat. No. 5,288,931.

EXAMPLE II

Figure 2:
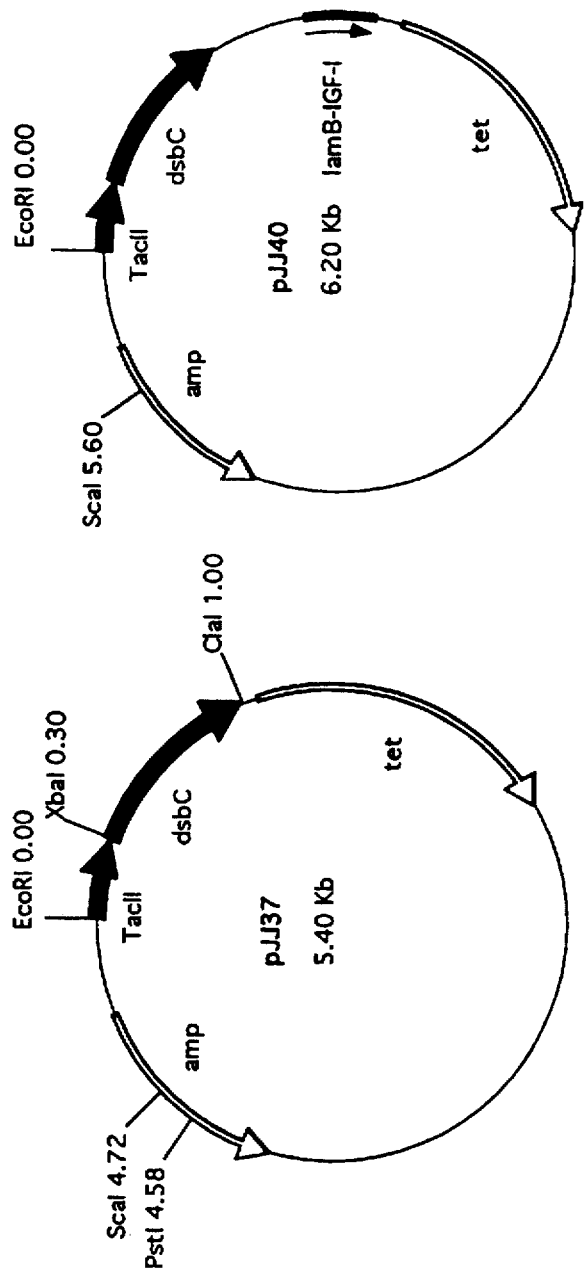
FIG. 2 depicts the construction of plasmid pJJ40, used to produce IGF-I.

The dsbC nucleotide sequence was amplified using PCR techniques from the genome of *E. coli* (Missiakas et al., supra, [1994]) and a XbaI site was added at the 5' end and a ClaI site at the 3' end of the DsbC-encoding sequence. This DNA fragment was digested with the appropriate restriction enzymes and ligated with a 1.0-kb PstI-XbaI fragment of pKMTacII (de Boer et al., *Proc. Natl. Acad. Sci. USA*, 80: 21–25 [1983]) and a 3.6-kb ClaI-PstI fragment of pBKIGF-2B (U.S. Pat. No. 5,342,763). The resulting plasmid, pJJ37 (see FIG. 2), contains dsbC under the control of the tacII promoter and confers resistance to ampicillin and tetracycline. This plasmid was digested with ClaI and the ends were filled in by Klenow fragment and deoxynucleotides.

After inactivation of the Klenow fragment and extraction of the digested DNA, the DNA was subsequently digested with ScaI and the 1.5-kb fragment containing the 5' end of the β-lactamase gene and the TacII-dsbC element was purified. This was ligated with a 4.6-kb fragment of EcoRI-digested and filled-in pBKIGF-2B, which had also been digested with ScaI. This fragment of pBKIGF-2B contained the 3' end of the β-lactamase, allowing selection for resistance to ampicillin as well as the DNA sequences for resistance to tetracycline and production of IGF-I. This plasmid is denoted pJJ40 (see FIG. 2).

This plasmid pJJ40 was transformed into *E. coli* strain 33D3, described above. 33D3 cells containing pJJ40 were then grown in a 10-liter fermentor under conditions identical to IGF-I production as described in U.S. Pat. No. 5,304,472, Example II, 1×feed conditions. When the optical density ($A_{550}$) of the culture reached 60, 1% lactose was added to induce the tacII promoter, thereby increasing dsbC expression. The growth medium was designed for phosphate depletion and phoA promoter induction to occur at an optical density ($A_{550}$) of 80 to 100. Total IGF-I production was measured by an HPLC assay described by U.S. Pat. No. 5,304,472.

The results are that the experiment with 1% lactose produced 4 g/L IGF-I, versus the control, pBKIGF-2B, no inducer, shown in Table 1 above, which produced 3 g/L of IGF-I. The correctly folded IGF-I can be recovered in high yield by liquid-liquid extraction followed by aerobic refolding as described above.

EXAMPLE III

Figure 3:
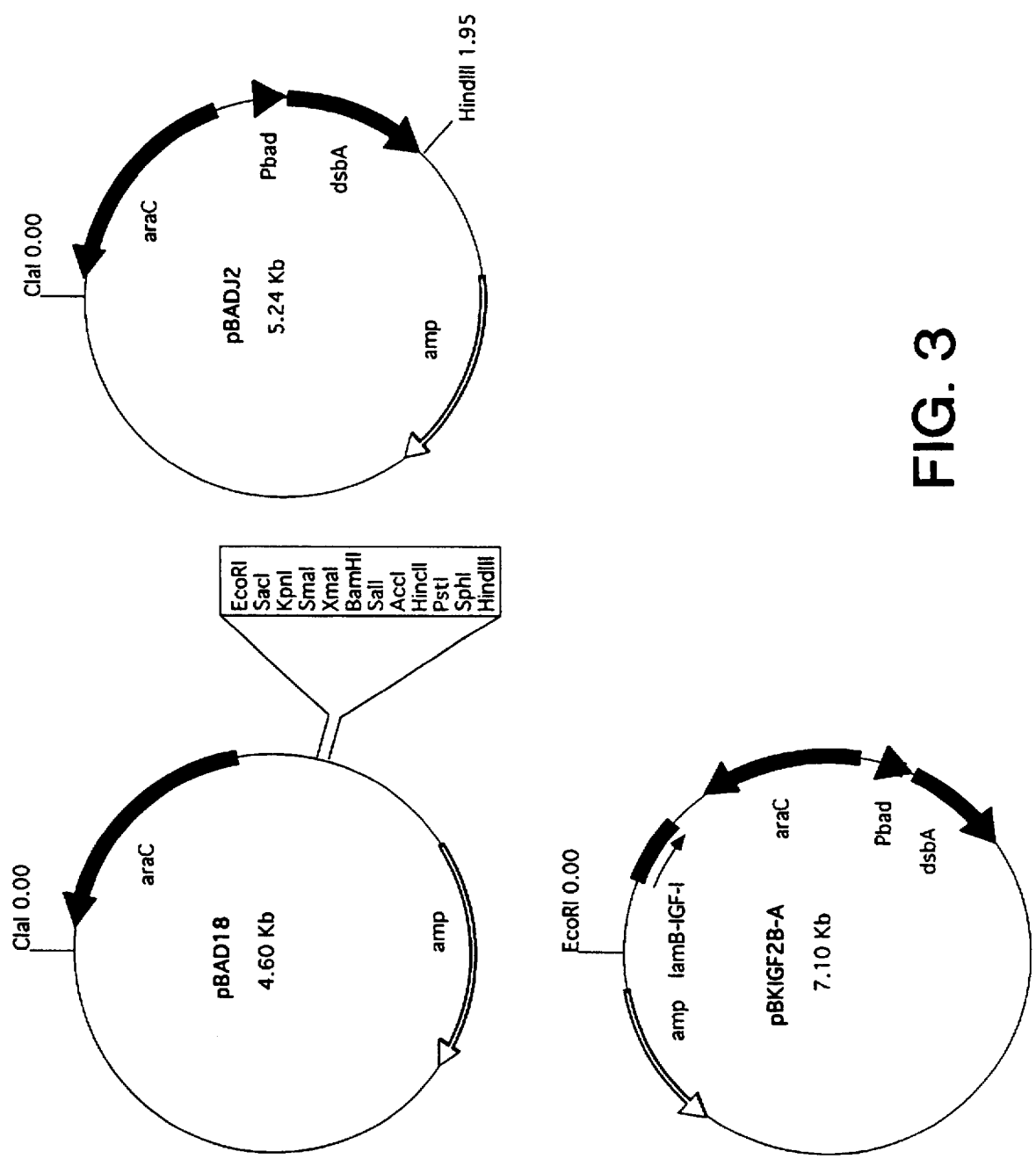
FIG. 3 depicts the construction of plasmid pBKIGF2B-A, used to produce IGF-I.

The dsbA gene was cloned into a vector pBAD18 (FIG. 3) containing a cloned inducible arabinose promoter (Guzman et al., supra) that over-expresses the gene in response to the presence of arabinose in the medium. The dsbA gene was amplified by PCR, which attached restriction sites at the ends for ease in cloning. An EcoRI site was placed at the 5' end and a KpnI site at the 3' end. The vector into which dsbA was cloned was digested with the same enzymes and the dsbA PCR product was ligated with the digested vector to form pBADJ2 (FIG. 3). This plasmid pBADJ2 was digested with ClaI and HindIII and then made blunt-ended with the use of Klenow polymerase fragment I. A 1.9-kb fragment encoding the arabinose promoter and dsbA was purified. This arabinose promoter with the dsbA gene was then cloned into the EcoRV site of the IGF-I production plasmid pBKIGF-2B as described above. The direction of transcription of dsbA was the same as for IGF-I. This plasmid was designated as pBKIGF2B-A.

The plasmid pBKIGF2B-A was then transformed into *E. coli* strain 36F8 (with the genotype W3110 tonA phoA Δ(argF-lac) ptr3 degP kan$^R$ ilvG+, and being temperature resistant at 37° C.). This strain was constructed in several steps using the same basic techniques described above. The starting host for the construction 27A7, is described in detail in U.S. Pat. No. 5,304,472.

Next, the degP41 kan$^r$ mutation was introduced into 27A7. This mutation is described in U.S. Pat. No. 5,304,472. The resulting strain is designated 27B4. The 27B4 strain grows poorly on LB media at 37° C. and 42° C. A temperature-resistant isolate was obtained at 37° C. by picking a spontaneous colony that grew better. This strain is designated 35E7.

A ribose deletion was then introduced into strain 35E7 by P1 cotransduction with a linked Tn10 insertion in the ilv gene. The isoleucine/valine auxotrophy was transduced to prototrophy using P1 phage grown on a strain carrying the ilvG2096$^R$ mutation (Lawther et al., *Proc. Natl. Acad. Sci. USA*, 78: 922–925 [1981]), which repairs a frameshift that causes the wild-type *E. coli* K-12 strain to be sensitive to valine. The ilv2096$^R$ locus was confirmed by resistance of the 36F8 host to 40 μg/mL valine. The rbs deletion was also repaired during this step, resulting in a strain able to utilize ribose as a carbon source.

The final strain 36F8 is resistant to T1 and Ø80 phage, lacks two proteases, does not overproduce alkaline phosphatase upon depletion of phosphate in the medium, grows well at 37° C., and is not susceptible to valine toxicity. 36F8 cells containing the plasmid pBKIGF2B-A were then grown in a 10-liter fermentor under conditions identical to the IGF-I production described in U.S. Pat. No. 5,304,472, supra, 1×feed conditions, Example III. When the optical density ($A_{550}$) of the culture reached 80, 1% (w/v) L-arabinose was added. This induced dsbA expression and resulted in secretion of the DsbA protein into the periplasm. The growth medium was designed for phosphate depletion and phoA promoter induction to occur at an optical density ($A_{550}$) of 100. Total IGF-I production was measured by the HPLC assay used in Example I.

The results are shown in Table 2 below:

TABLE 2

| Fermentation Run | Conditions | g/L IGF-I |
|---|---|---|
| 1 | pBKIGF2B-A, 1.5% arabinose | 6.1 |
| 2 | pBKIGF2B-A, 1.0% arabinose | 7.6 |
| 3 | pBKIGF2B-A, 1.0% arabinose | 7.2 |
| 4 | pBKIGF2B-A, 0.5% arabinose | 6.6 |

TABLE 2-continued

| Fermentation Run | Conditions | g/L IGF-I |
|---|---|---|
| 5 | typical periplasmic IGF-I process | 3.7 |

The results show that over-expression of the dsbA gene in the periplasm of the bacteria improves yield of total (soluble and insoluble) IGF-I for all runs involving the arabinose promoter and DsbA. This increase in IGF-I accumulation was approximately 2-fold using 1% L-arabinose. The IGF-I in correctly folded form can be recovered by liquid-liquid extraction and by refolding as described above, or by methods as described in U.S. Pat. No. 5,288,931.

The yield increase was not seen for DsbB, as cells over-expressing dsbB from a very similar plasmid do not show the increase. Furthermore, if the dsbA DNA and IGF-I DNA were co-expressed using the same promoter, total IGF-I yields were decreased as compared to a control with no dsbA gene (pRKIGF-2B).

EXAMPLE IV

For further exploration of the potential advantages of DsbA over-expression, a host organism with a mutated phoS protein (as described in U.S. Pat. No. 5,304,472) was employed in the process. After the phosphate feed rate was adjusted, IGF-I polypeptide yields in excess of 9 g/L were obtained.

Figure 4:
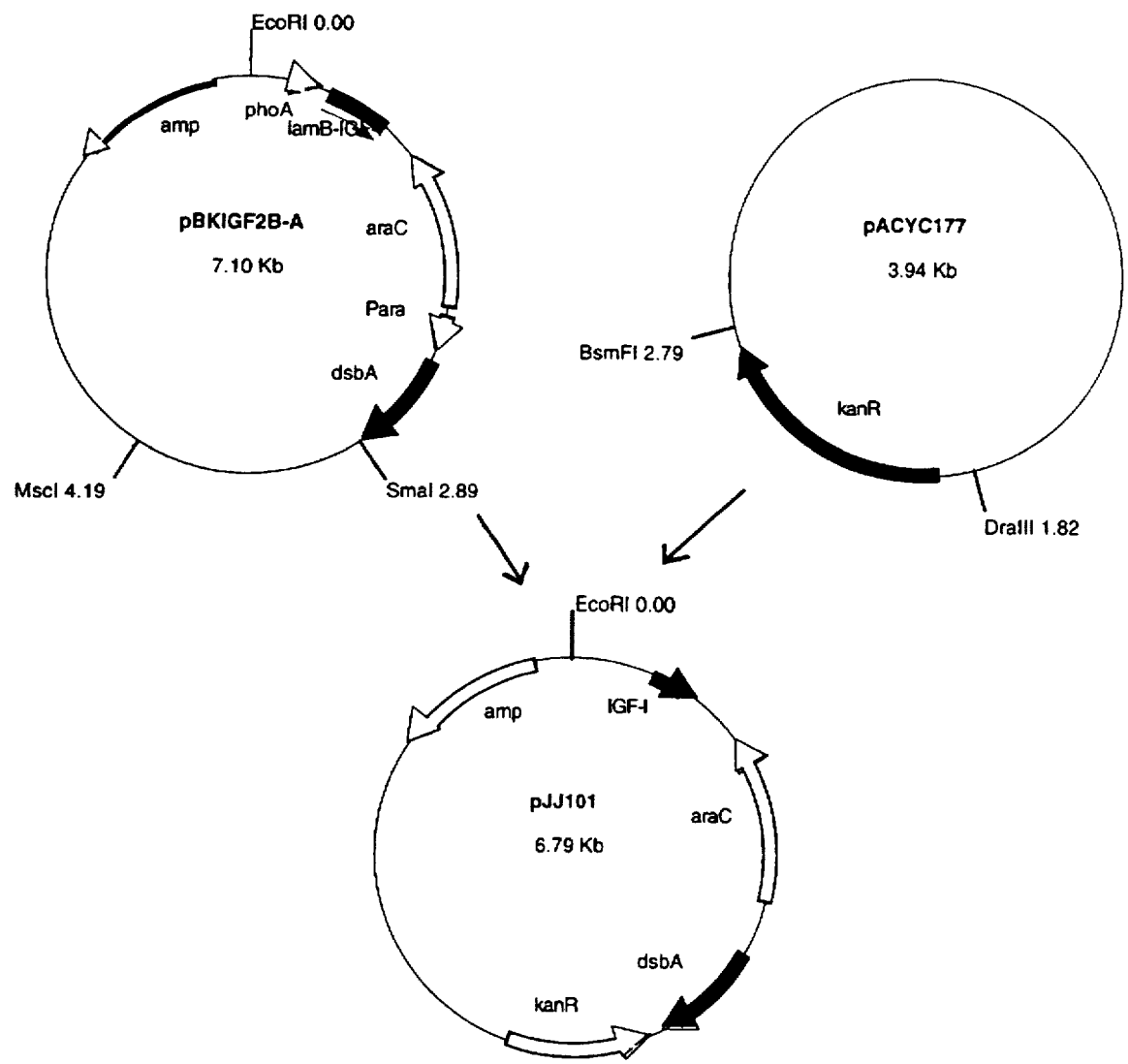
FIG. 4 depicts the construction of plasmid pJJ101, used to produce IGF-I.

In this study, the plasmids used were pBKIGF-2B (U.S. Pat. No. 5,342,763) and pJJ101. Plasmid pJJ101 (FIG. 4) was constructed to allow the expression of dsbA from the arabinose promoter and to use kanamycin as the drug resistance marker for plasmid introduction and retention. It was constructed as follows: A 973-bp DraIII-BsmFI fragment from pACYC177 (Chang and Cohen, *J. Bacteriology*, 134: 1141–1156 [1978]) was ligated to a 5820-bp MscI-SmaI fragment from pBKIGF2B-A described above. The resulting plasmid pJJ101 is both kanamycin and ampicillin resistant. The kanamycin resistance is derived from the pACYC177 fragment. The IGF-I gene, arabinose-regulated dsbA element, and ampicillin resistance gene are derived from pBKIGF2B-A.

Two different host organisms were used in this study, 45F8 and 46D5. The genotype of 45F8 is *E. coli* K12 W3110 ΔtonA ptr3 Δ(argF-lac) 169 degP41 (ΔPstI-kan$^s$) ΔompT ilvG2096$^R$ phoS* (T10Y). 46D5 is similar, but, in addition, contains the following loci, Δcyo::kan$^r$ rhaR Δ(rbs7). RhaR and Δ(rbs7) are a point mutation and a deletion which render the organism unable to use rhamnose and ribose. These changes are invisible unless ribose or rhamnose are present. They have been shown to have no effect on the yield of IGF-I polypeptide. The Δcyo::kan$^r$ mutation removes one of the cytochrome oxidases, cytochrome o oxidase. However, the other, cytochrome d oxidase, is sufficient for normal metabolism and has been shown to have little or no effect on the yield of IGF-I polypeptide. The details of the construction of these strains are provided below.

The host 46D5 is a derivative of *E. coli* K12 W3110, described above. The complete genotype of 46D5 is IN(rrnD-rrnE)1 ΔfhuA ptr3 Δ(argF-lac)169 ΔompT degP41 (ΔPstI-kan$^s$) phoS* (T10Y) cyo::kan$^r$ rhaR Δ(rbs7) ilvG2096$^R$. The derivation of 46D5, diagrammed in Table 3, is described below.

The starting strain, *E. coli* W3110, is a derivative of *E. coli* K-12 that is F$^-$ and Λ$^-$. It has been shown to carry an inversion of the chromosome between rrnD and rrnE. Bachmann et al., supra, and Bachmann, supra.

The fhuA gene (previously designated tonA) (U.S. Pat. No. 5,304,472) was deleted from W3110 by imprecise excision of Tn10 following its insertion into the fhuA gene. The resulting strain, 1A2, is resistant to bacteriophages T1, T5, and Φ80.

The ptr3 gene (U.S. Pat. No. 5,304,472) was introduced into this strain by two steps. Two flanking markers, thyA8 and argA81::Tn10 were transferred into 1A2. Transduction with P1 phage grown on a ptr3 mutant resulted in the introduction of the ptr3 mutation simultaneously with the conversion of thyA8 and argA81::Tn10 to wild-type loci. This strain, 9E4, lacks periplasmic protease III.

Two deletion mutations, phoAΔE15 and Δ(argF-lac)169 (U.S. Pat. No. 5,304,472) were simultaneously introduced into W3110 by P1 cotransduction with a linked Tn5 insertion in the proC gene. P1 transduction to proline prototrophy restored the proC gene. The phoAΔE15 mutation eliminates alkaline phosphatase expression, and the Δ(argF-lac)169 mutation is responsible for the lac-minus phenotype of this strain, 27A7.

The ompT deletion (U.S. Pat. No. 5,304,472) was introduced by P1 cotransduction with a linked Tn10 insertion in the purE gene. Next, this strain was transduced to purine prototrophy to remove the transposon. The presence of the ompT deletion was confirmed by colicin B and colicin D resistance in this strain, 27C6. This strain lacks the outer membrane protease VII which is encoded by the ompT gene.

The degP41(ΔPstI-kan$^r$) (U.S. Pat. No. 5,304,472) mutation in the gene for a periplasmic protease was introduced by transduction. This mutation was constructed in vitro by replacing a section of the degP gene with a kanamycin-resistance gene. This is not a transposon, but allows for selection of the deletion using kanamycin resistance. The resulting strain is 27C7.

A Tn10 insertion in the ilv gene was introduced by P1 transduction. The isoleucine/valine auxotrophy was transduced to prototrophy using P1 phage grown on a strain carrying the ilvG2096$^R$ mutation (Lawther et al., Proc. Natl. Acad. Sci. USA, 78: 922–925 [1981]), which repairs a frameshift that causes the wild-type E. coli K-12 to be sensitive to valine. The ilvG2096$^R$ locus was confirmed by the resistance of the 43D3 host to 40 µg/mL valine (0.3 mM).

The degP41(ΔPst1-kan$^r$) mutation was replaced using P1 transduction with a degP41(ΔPst1-kan$^s$) mutation. A pro-AB::Tn10 which is linked to degP was introduced into 43D3. The proline auxotroph was transduced to prototrophy using P1 phage grown on a strain carrying the degP kan$^s$ mutation. Since degP is linked by cotransduction to fhuA, the new strain, 43E7, was confirmed to retain resistance to bacteriophage T1.

The wild-type alkaline phosphatase gene was re-introduced into this host background to capitalize on the benefits obtained from the phoS* mutation described below. P1 co-transduction of a Tn5 insertion in the proC gene with phoA+ was used to reintroduce the wild-type alkaline phosphatase gene into this host background. P1 transduction to proline prototrophy restored the proC gene. The resulting strain, 44D6, regained alkaline phosphatase expression and maintained the Δ(argF-lac) mutation responsible for the lac⁻ phenotype.

A mutation which results in an altered phosphate-binding protein, phoS* (T10Y) (U.S. Pat. No. 5,304,472) was introduced. The phoS* protein has a reduced affinity for phosphate in the medium. The result is that induction of the alkaline phosphatase promoter occurs at a higher phosphate concentration than the wild-type. This allows product expression from the APase promoter without severely depriving the culture of phosphate. PhoS is linked by P1 cotransduction to ilv. A Tn10 insertion in the ilv gene was re-introduced by P1 transduction. The isoleucine/valine auxotrophy was transduced to prototrophy using P1 phage grown on a strain carrying the phoS* (T10Y) and ilvG2096$^R$ mutations. The presence of the phoS* mutation results in blue colonies on high-phosphate agar media containing the chromogenic substrate, XP. The resulting strain was 45F8.

The cyo::kan$^r$ (Oden et al., Gene, 96: 29–36 [1990]) mutation in the gene for cytochrome o oxidase was introduced by transduction. This mutation was constructed in vitro by replacing a portion of the cyo gene with a kanamycin-resistance gene. Introduction of this mutation prevents switching between the low- and high-affinity cytochrome oxidases, cyo and cyd, respectively. The cytochrome switching phenomenon can lead to dissolved oxygen instabilities and unsuccessful fermentation runs. The resulting strain was 45F9.

Finally, two mutations in carbohydrate utilization pathways were introduced. The rhaR (Moralejo et al., J. Bacteriol., 175: 5585–5594 [1993]) mutation was introduced by P1 co-transduction with argE. An argE::Tn10 was introduced. The strain was restored to prototrophy using P1 phage grown on a strain carrying the rhaR mutation. The resulting strain, 46F1, was confirmed to be unable to utilize rhamnose as a carbon source.

The Δrbs7 (Lopilato et al., J. Bacteriol., 158: 665–673 [1984]) mutation was introduced by P1 cotransduction with a linked Tn10 insertion in the ilv gene. The isoleucine/valine auxotrophy was transduced to prototrophy using P1 phage on a strain carrying the ilvG2096$^R$ mutation. The presence of the ribose-utilization defect in the resulting strain, 46D5, was confirmed using minimal media containing ribose as a carbon source. Retention of the phoS* (T10Y) was also confirmed as described above.

The important characteristics of the final strain, 46D5, are that it is resistant to T1 and Φ80 phage, lacks three proteases, is not susceptible to valine toxicity, does not undergo cytochrome switching, and allows phoA promoter induction at higher phosphate concentrations.

Table 3 indicates the strains and genotypes involved in the construction of 46D5.

TABLE 3

| Strain | Genotype |
| --- | --- |
| W3110 | K-12 F⁻ lambda⁻ IN(rrnD-rrnE)1 |
| 1A2 | W3110 ΔfhuA |
| 9E4 | W3110 ΔfhuA ptr3 |
| 27A7 | W3110 ΔfhuA ptr3 phoAΔE15 Δ(argF-lac)169 |
| 27C6 | W3110 ΔfhuA ptr3 phoAΔE15 Δ(argF-lac)169 ΔompT |
| 27C7 | W3110 ΔfhuA ptr3 phoAΔE15 Δ(argF-lac)169 ΔompT degP41 (ΔpstI-kan$^r$) |
| 43D3 | W3110 ΔfhuA ptr3 phoAΔE15 Δ(argF-lac)169 ΔompT degP41 (ΔPst1-kan$^r$) ilvG2096$^R$ |
| 43E7 | W3110 Δ(argF-lac)169 ΔompT ΔfhuA ptr3 phoAΔE15 degP41 (ΔPst1-kan$^s$) ilvG2096$^R$ |
| 44D6 | W3110 ΔfhuA ptr3 Δ(argF-lac)169 degP41(Δpst1-kan$^s$) ΔompT ilvG2096$^R$ |
| 45F8 | W3110 ΔfhuA ptr3 Δ(argF-lac)169 degP41 (Δpst1-kan$^s$) ΔompT phoS* (T10Y) ilvG2096$^R$ |
| 45F9 | W3110 ΔfhuA ptr3 Δ(argF-lac)169 degP41(Δpst1-kan$^s$) ΔompT ilvG2096$^R$ phoS*(T10Y) Δcyo::kan$^r$ |
| 46F1 | W3110 ΔfhuA ptr3 Δ(argF-lac)169 degP41(Δpst1-kan$^s$) ΔompT ilvG2096$^R$ phoS*(T10Y) Δcyo::kan$^r$ |

TABLE 3-continued

| Strain | Genotype |
|---|---|
| 46D5 | rhaR<br>W3110 ΔfhuA ptr3 Δ(argF-lac)169 degP41(Δpst1-kan$^r$) ΔompT ilvG2096$^R$ phoS*(T10Y) Δcyo::kan$^r$ rhaR Δ(rbs7) |

The fermentations were conducted essentially as described in U.S. Pat. No. 5,304,472, Example III, 1×feed conditions. However, in all cases the complex nitrogen feed was started at the beginning of the fermentation and no isoleucine was added to the medium. In most cases, a 70% wt/vol glucose feed was used, but for SI1339 and SI1341, a 85% wt/vol glucose feed was employed. In all cases with the plasmid pJJ101, DsbA expression was induced by adding arabinose to the culture to produce a 1% concentration at a cell density of 80 OD ($A_{550}$) No induction was done for the control case (run SI1312). Run SI1341 was conducted at a higher agitation rate (1100 to 1200 rpm) as compared to the other fermentations, which were all conducted at 1000 rpm. Table 4 provides a summary of the experiments as well as peak titers. The time course of IGF-I polypeptide accumulation for each is shown in FIG. 5.

TABLE 4

| Run No. | Organism | Complex N Feed Rates (mL/min) | | RPM | Glucose Feed (wt %) | Peak Titers (g/L) |
|---|---|---|---|---|---|---|
| | | Initial | After 120 OD | | | |
| SI1312 | 46D5/pBKIGF-2B | 0.5 | 0.25 | 1000 | 70 | 6.4 |
| SI1306 | 45F8/pJJ101 | 0.5 | 0.25 | 1000 | 70 | 7.8 |
| SI1329 | 45F8/pJJ101 | 0.5 | 0.5 | 1000 | 70 | 9.0 |
| SI1339 | 45F8/pJJ101 | 0.6 | 0.6 | 1000 | 85 | 9.6 |
| SI1341 | 45F8/pJJ101 | 0.6 | 0.6 | 1100–1200 | 85 | 9.3 |

In all cases with dsbA over-expression, the rate of IGF-I polypeptide accumulation and the final titer are significantly improved relative to the case without dsbA overexpression. Furthermore, in comparison to the results in Example III, significantly higher titers are obtained when a host with a phoS mutation and an active phoA gene is combined with dsbA overexpression for the production of IGF-I polypeptide.

What is claimed is:

1. A process for producing a heterologous polypeptide in bacteria comprising:
   (a) culturing bacterial cells that lack their native pstS gene and comprise nucleic acid encoding a PstS variant having an amino acid variation within the phosphate-binding region of the corresponding native PstS, nucleic acid encoding a DsbA or DsbC protein, nucleic acid encoding the heterologous polypeptide, a signal sequence for secretion of both the DsbA or DsbC protein and the heterologous polypeptide, an inducible promoter for the nucleic acid encoding the DsbA or DsbC protein, and an alkaline phosphatase promoter for the nucleic acid encoding the heterologous polypeptide, wherein the nucleic acid encoding a PstS variant is under the transcriptional control of the wild-type pstS gene promoter, and wherein the culturing takes place under conditions whereby expression of the nucleic acid encoding the DsbA or DsbC protein is induced prior to induction of the expression of the nucleic acid encoding the heterologous polypeptide, under conditions whereby the culturing takes place in a culture medium at a concentration of inorganic phosphate in the medium that during all phases of cell growth is above the level at which the cells are starved for phosphate, and under conditions whereby either both the heterologous polypeptide and the DsbA or DsbC protein are secreted into the periplasm of the bacteria or the heterologous polypeptide is secreted into the medium in which the bacterial cells are cultured; and
   (b) recovering the heterologous polypeptide from the periplasm or the culture medium.

2. The process of claim 1 wherein the heterologous polypeptide is a mammalian polypeptide.

3. The process of claim 2 wherein the mammalian polypeptide is a human polypeptide.

4. The process of claim 3 wherein the human polypeptide is insulin-like growth factor-I.

5. The process of claim 1 wherein the concentration of inorganic phosphate at all phases of cell growth is more than about 0.5 mM and wherein the pstS variant is homologous to the native pstS gene in the host cells.

6. The process of claim 1 wherein the heterologous is recovered from the periplasm of the bacterial cells.

7. The process of claim 1 wherein the bacterial cells are Enterobacteriaceae cells.

8. The process of claim 1 wherein the amino acid variation in the nucleic acid molecule is an amino acid substitution.

9. The process of claim 8 wherein the bacterial cells are E. coli and a hydrophobic residue is substituted for threonine at position 10 of the phosphate-binding region of native E. coli PstS.

10. The process of claim 8 wherein the nucleic acid encoding a PstS variant encodes T10F PstS under the transcriptional control of the wild-type E. coli pstS gene promoter.

11. The process of claim 8 wherein the nucleic acid encoding a PstS variant encodes T10L PstS under the transcriptional control of the wild-type E. coli pstS gene promoter.

12. The process of claim 8 wherein the nucleic acid encoding a PstS variant encodes T10M PstS under the transcriptional control of the wild-type E. coli pstS gene promoter.

13. The process of claim 8 wherein the nucleic acid encoding a PstS variant encodes T10Y PstS under the transcriptional control of the wild-type E. coli pstS gene promoter.

14. The process of claim 8 wherein the nucleic acid encoding a PstS variant encodes T10A PstS under the transcriptional control of the wild-type E. coli pstS gene promoter.

15. The process of claim 8 wherein the nucleic acid encoding a PstS variant encodes T10C PstS under the transcriptional control of the wild-type E. coli pstS gene promoter.

16. The process of claim 8 wherein the nucleic acid encoding a PstS variant encodes T10G PstS under the transcriptional control of the wild-type E. coli pstS gene promoter.

17. The process of claim 8 wherein the nucleic acid encoding a PstS variant encodes S38F PstS under the transcriptional control of the wild-type E. coli pstS gene promoter.

18. The process of claim 8 wherein the nucleic acid encoding a PstS variant encodes D56V PstS under the transcriptional control of the wild-type E. coli pstS gene promoter.

19. The process of claim 8 wherein the nucleic acid encoding a PstS variant encodes D56A PstS under the transcriptional control of the wild-type *E. coli* pstS gene promoter.

20. The process of claim 8 wherein the nucleic acid encoding a PstS variant encodes D56L PstS under the transcriptional control of the wild-type *E. coli* pstS gene promoter.

21. The process of claim 8 wherein the nucleic acid encoding a PstS variant encodes D56S PstS under the transcriptional control of the wild-type *E. coli* pstS gene promoter.

22. The process of claim 8 wherein the nucleic acid encoding a PstS variant encodes S139T PstS under the transcriptional control of the wild-type *E. coli* pstS gene promoter.

23. The process of claim 8 wherein the nucleic acid encoding a PstS variant encodes S139P PstS under the transcriptional control of the wild-type *E. coli* pstS gene promoter.

24. The process of claim 8 wherein the nucleic acid encoding a PstS variant encodes S139L PstS under the transcriptional control of the wild-type *E. coli* pstS gene promoter.

25. The process of claim 8 wherein the nucleic acid encoding a PstS variant encodes T141H PstS under the transcriptional control of the wild-type *E. coli* pstS gene promoter.

26. The process of claim 1 wherein the nucleic acid encoding the PstS variant is integrated into the chromosome thereof.

27. The process of claim 1 wherein nucleic acid encoding DsbA is expressed.

28. The process of claim 1 wherein after the polypeptide is recovered, the DsbA or DsbC protein is separated from the polypeptide.

29. The process of claim 1 wherein the bacterial cells are transformed with one or two expression vectors containing the nucleic acid encoding the DsbA or DsbC protein and the nucleic acid encoding the heterologous polypeptide.

30. The process of claim 29 wherein the bacterial cells are transformed with two vectors respectively containing the nucleic acid encoding the DsbA or DsbC protein and the nucleic acid encoding the heterologous polypeptide.

31. The process of claim 29 wherein the nucleic acid encoding the DsbA or DsbC protein and the nucleic acid encoding the heterologous polypeptide are contained on one vector with which the bacterial cells are transformed.

32. The process of claim 1 wherein the induction of expression of the nucleic acid encoding DsbA or DsbC is carried out by adding an inducer to the culture medium.

\* \* \* \* \*

UNITED STATES PATENT AND TRADEMARK OFFICE
CERTIFICATE OF CORRECTION

PATENT NO. : 5,789,199

DATED : August 4, 1998

INVENTOR(S) : Joly et al.

It is certified that error appears in the above-identified patent and that said Letters Patent is hereby corrected as shown below:

Column 34, claim 6, line 24, insert --polypeptide-- after "heterologous".

Signed and Sealed this

Twentieth Day of October, 1998

Attest:

BRUCE LEHMAN

*Attesting Officer*         *Commissioner of Patents and Trademarks*